US009433783B2

United States Patent
Wei et al.

(10) Patent No.: US 9,433,783 B2
(45) Date of Patent: *Sep. 6, 2016

(54) INCONTINENCE THERAPY

(71) Applicant: Medtronic, Inc., Minneapolis, MN (US)

(72) Inventors: Xuan K. Wei, Minnetonka, MN (US); Eric H. Bonde, Minnetonka, MN (US); Keith A. Miesel, St. Paul, MN (US); Mark S. Lent, Brooklyn Park, MN (US); Gregory F. Molnar, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/880,066

(22) Filed: Oct. 9, 2015

(65) Prior Publication Data

US 2016/0030741 A1    Feb. 4, 2016

Related U.S. Application Data

(63) Continuation of application No. 13/265,702, filed as application No. PCT/US2010/030559 on Apr. 9, 2010, now Pat. No. 9,155,885.

(60) Provisional application No. 61/172,584, filed on Apr. 24, 2009, provisional application No. 61/183,019, filed on Jun. 1, 2009.

(51) Int. Cl.
*A61N 1/00*    (2006.01)
*A61N 1/36*    (2006.01)
(Continued)

(52) U.S. Cl.
CPC .......... *A61N 1/36007* (2013.01); *A61N 1/0514* (2013.01); *A61N 1/36128* (2013.01); *A61N 1/37252* (2013.01)

(58) Field of Classification Search
CPC ..................... A61N 1/36007; A61N 1/36507; A61N 1/36107; A61N 1/0514; A61N 1/0524
See application file for complete search history.

(56) References Cited

U.S. PATENT DOCUMENTS

| 4,607,639 A | 8/1986 | Tanagho et al. |
| 4,739,764 A | 4/1988 | Lue et al. |

(Continued)

FOREIGN PATENT DOCUMENTS

| WO | 0154767 A1 | 8/2001 |
| WO | 2004093978 A1 | 11/2004 |
| WO | 2010123704 A2 | 10/2010 |

OTHER PUBLICATIONS

Prosecution History from U.S. Appl. No. 13/265,702, dated Oct. 21, 2011 through Jun. 8, 2015, 253 pp.

(Continued)

*Primary Examiner* — Mallika D Fairchild
(74) *Attorney, Agent, or Firm* — Shumaker & Sieffert, P.A.

(57) ABSTRACT

Techniques for managing urinary or fecal incontinence include delivering a first type of therapy to generate a first physiological response and, upon detecting a trigger event, delivering a second type of therapy to generate a second physiological response. The first type of therapy can be delivered on a substantially regular basis, while the second type of therapy is delivered as needed to provide an additional boost of therapy. The trigger event for activating the delivery of the second type of therapy may include input from a sensor that indicates a bladder condition, patient activity level or patient posture, or patient input. In some examples, the therapy is stimulation therapy.

25 Claims, 14 Drawing Sheets

(51) Int. Cl.
*A61N 1/05* (2006.01)
*A61N 1/372* (2006.01)

(56) References Cited

U.S. PATENT DOCUMENTS

| | | |
|---|---|---|
| 6,266,557 B1 | 7/2001 | Roe et al. |
| 6,449,512 B1 | 9/2002 | Boveja |
| 6,652,449 B1 | 11/2003 | Gross et al. |
| 6,735,474 B1 | 5/2004 | Loeb et al. |
| 6,907,293 B2 | 6/2005 | Grill et al. |
| 6,941,171 B2 | 9/2005 | Mann et al. |
| 6,990,376 B2 | 1/2006 | Tanagho et al. |
| 7,047,078 B2 | 5/2006 | Boggs, II et al. |
| 7,276,057 B2 | 10/2007 | Gerber |
| 7,280,867 B2 | 10/2007 | Frei et al. |
| 7,489,970 B2 | 2/2009 | Lee et al. |
| 7,505,815 B2 | 3/2009 | Lee et al. |
| 7,548,786 B2 | 6/2009 | Lee et al. |
| 8,521,292 B2 | 8/2013 | Wei et al. |
| 2003/0100930 A1 | 5/2003 | Cohen et al. |
| 2004/0199218 A1 | 10/2004 | Lee et al. |
| 2005/0060005 A1 | 3/2005 | Boggs, II et al. |
| 2005/0070969 A1* | 3/2005 | Gerber ............... A61N 1/36071 607/40 |
| 2005/0222636 A1* | 10/2005 | Grill .................... A61N 1/0556 607/39 |
| 2005/0261746 A1 | 11/2005 | Gross et al. |
| 2006/0020297 A1 | 1/2006 | Gerber et al. |
| 2006/0190046 A9 | 8/2006 | Gerber |
| 2006/0190047 A1 | 8/2006 | Gerber et al. |
| 2006/0190048 A1 | 8/2006 | Gerber |
| 2006/0190049 A1 | 8/2006 | Gerber et al. |
| 2006/0195152 A1 | 8/2006 | Gerber |
| 2006/0247723 A1 | 11/2006 | Gerber et al. |
| 2006/0259099 A1 | 11/2006 | Goetz et al. |
| 2006/0293719 A1 | 12/2006 | Naghavi |
| 2007/0027494 A1 | 2/2007 | Gerber |
| 2007/0027495 A1 | 2/2007 | Gerber |
| 2007/0100387 A1 | 5/2007 | Gerber |
| 2007/0100388 A1 | 5/2007 | Gerber |
| 2007/0293906 A1 | 12/2007 | Cowan et al. |
| 2008/0294226 A1 | 11/2008 | Moffitt et al. |
| 2008/0300650 A1 | 12/2008 | Gerber et al. |
| 2009/0036946 A1 | 2/2009 | Cohen et al. |
| 2009/0138061 A1 | 5/2009 | Stephens et al. |
| 2009/0222058 A1 | 9/2009 | Craggs |
| 2009/0306460 A1 | 12/2009 | Stephens et al. |
| 2010/0094372 A1 | 4/2010 | Grill et al. |

OTHER PUBLICATIONS

International Preliminary Report on Patentability from International Application No. PCT/US2010/030559, mailed Oct. 25, 2011, 11 pp.
International Search Report and Written Opinion of International Application No. PCT/US2010/030559, mailed Nov. 10, 2010, 20 pp.

* cited by examiner

INCONTINENCE THERAPY

This application is a continuation application of U.S. patent application Ser. No. 13/265,702, filed on Oct. 21, 2011, which is a National Stage Entry under 35 U.S.C. §371 of PCT Application No. PCT/US2010/030559, filed on Apr. 9, 2010, which claims priority to U.S. Provisional Application No. 61/183,019, filed on Jun. 1, 2009 and U.S. Provisional Application No. 61/172,584, filed on Apr. 24, 2009. The entire contents of application Ser. No. 13/265,702, PCT/US2010/030559, 61/183,019, and 61/172,584 are incorporated herein by reference.

TECHNICAL FIELD

The disclosure relates to implantable medical devices and, more particularly, medical devices for the treatment of urinary or fecal incontinence.

BACKGROUND

Urinary incontinence, or an inability to control urinary function, is a problem that afflicts people of all ages, genders, and races. Various muscles, nerves, organs and conduits within the pelvic floor cooperate to collect, store and release urine. A variety of disorders may compromise urinary tract performance, and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients may also suffer from nerve disorders that prevent proper triggering and operation of the bladder, sphincter muscles or nerve disorders that lead to overactive bladder activities. Nerves running though the pelvic floor stimulate contractility in the sphincter. An improper communication between the nervous system and the urinary sphincter can result in urinary incontinence.

SUMMARY

Techniques for managing urinary or fecal incontinence are described. According to one example, an implantable medical device (IMD) delivers first stimulation therapy to generate a first physiological response that helps prevent the occurrence of an involuntary voiding event and a second stimulation therapy to generate a second physiological response that helps prevent the occurrence of an involuntary voiding event. The first and second physiological responses are different, and in some examples, involve the activation of different muscles.

The IMD delivers the first stimulation therapy on a regular basis, e.g., to reduce bladder contractions, and, when triggered, delivers the second stimulation therapy, e.g., to promote closure of a urinary or anal sphincter. The IMD delivers the second stimulation therapy upon the detection of a patient parameter indicative of a high probability that an involuntary voiding event will occur or based on patient input. The second stimulation therapy provides a safeguard in addition to the primary incontinence therapy (i.e., the first stimulation therapy) against the occurrence of an involuntary voiding event. Thus, the second stimulation therapy provides an increased protection against the occurrence of involuntary voiding events when needed or desired.

In one aspect, the disclosure is directed to a method comprising delivering, with a medical device, a first electrical stimulation therapy to a patient to generate a first physiological effect, receiving input from the patient or a sensor while the medical device is delivering the first electrical stimulation therapy, and delivering, with a second medical device, a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence. The first and second electrical stimulation therapies can be delivered at substantially the same time or at different times, which do not overlap.

In another aspect, the disclosure is directed to a method comprising controlling, with a processor, a medical device to deliver a first electrical stimulation therapy to a patient to generate a first physiological effect, receiving input from the patient or a sensor, and controlling, with the processor, the medical device to deliver a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence.

In another aspect, the disclosure is directed to a medical system comprising a therapy delivery module that generates and delivers a first electrical stimulation therapy to a patient to generate a first physiological effect and a second electrical stimulation therapy to the patient to generate a second physiological effect that is different than the first physiological effect, and a processor that controls the therapy delivery module to deliver the second stimulation therapy based on received input, wherein the first and second electrical stimulation therapies are configured to manage one of urinary incontinence or fecal incontinence.

In another aspect, the disclosure is directed to a medical system comprising means for delivering a first electrical stimulation therapy to a patient to generate a first physiological effect, means for receiving input from the patient or a sensor, and means for delivering a second electrical stimulation therapy to the patient to generate a second physiological effect that is different than the first physiological effect based on the input from the patient or the sensor, wherein the first and second electrical stimulation therapies are configured to manage one of urinary incontinence or fecal incontinence.

In another aspect, the disclosure is directed to a computer-readable medium containing instructions. The instructions cause a programmable processor to control a therapy delivery module (e.g., of a medical device) to deliver a first electrical stimulation therapy to a patient to generate a first physiological effect and deliver a second electrical stimulation therapy to the patient to generate a second physiological effect that is different than the first physiological effect based on received input (e.g., patient input or input from a sensor indicative of patient activity, posture or bladder condition). The first and second electrical stimulation therapies are configured to manage one of urinary incontinence or fecal incontinence.

In another aspect, the disclosure is directed to an article of manufacture comprising a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

DETAILED DESCRIPTION

Figure 1:
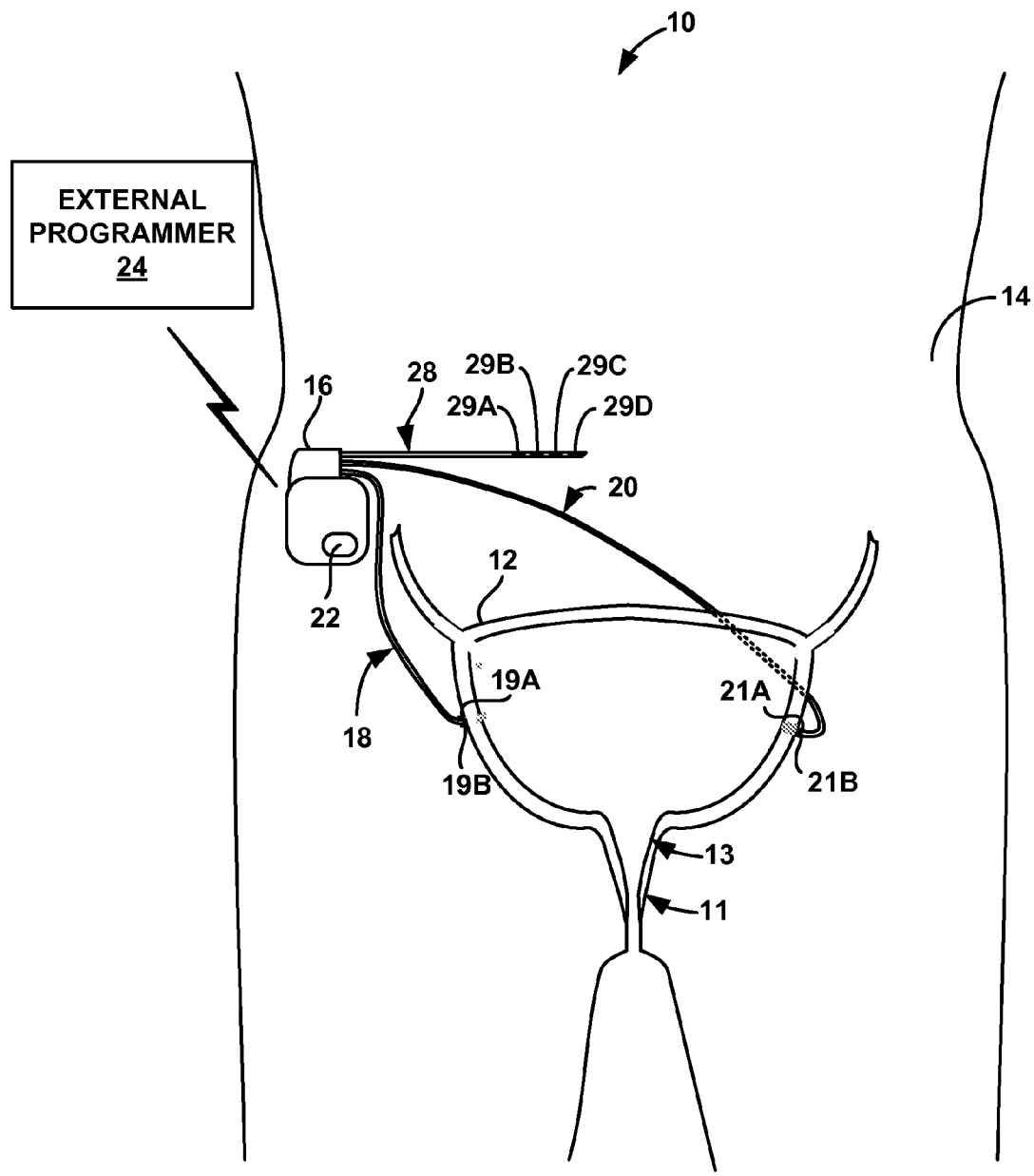
FIG. 1 is a conceptual diagram illustrating an example therapy system that delivers a first stimulation therapy to a patient and, when triggered, a second stimulation therapy to manage urinary incontinence.

Urinary incontinence refers to a condition of involuntary loss of urine, and may include urge urinary incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence, and disorders in which urination does not occur as desired, such as urinary retention disorder. Stress or urge incontinence may also be referred to as overactive bladder or as leading to overactive bladder activities. Although therapies for treating urinary incontinence, such as electrical stimulation to the bladder for fluid retention, are effective, involuntary events may still occur.

One type of therapy for treating urinary incontinence includes delivery of electrical stimulation. For example, delivery of electrical stimulation from an implantable medical device to nerves in the pelvic floor, such as the sacral nerve, pudendal nerve, dorsal genital nerve, or branches of any of the aforementioned nerves may provide an effective therapy for urinary incontinence. Electrical stimulation of the sacral nerve may modulate afferent nerve activities to restore urinary function. In addition, electrical stimulation of the nerves innervating pelvic floor muscles may strengthen pelvic floor muscle and promote urinary continence.

Techniques described in this disclosure include delivering a first electrical stimulation therapy to a patient to generate a first physiological effect to manage urinary or fecal incontinence and, when triggered, delivering a second electrical stimulation therapy to generate a second physiological effect that further helps to prevent an occurrence of an involuntary urinary or fecal voiding event. The second stimulation therapy may, therefore, provide an additional safeguard against the occurrence of an involuntary voiding event in situations in which the involuntary voiding event may be likely to occur. In some cases, only the second stimulation therapy is delivered to the patient to manage urinary or fecal incontinence.

The first stimulation therapy may be a chronic (e.g., non-temporary) therapy delivered to the patient to control urinary or fecal incontinence. In general, the first electrical stimulation therapy is delivered on a substantially regular basis to manage patient incontinence. In some examples, the first electrical stimulation is delivered to a patient in an open loop, i.e., without the use of an external feedback mechanism such as a sensor. However, in some cases, a sensor signal or patient input may be used to adjust the stimulation parameters of the first stimulation therapy.

The second electrical stimulation therapy may be referred to as a temporary stimulation therapy because the second electrical stimulation therapy is delivered for a predetermined period of time (duration of time), rather than on a regular basis. In some examples, the predetermined period of time may be controlled by the patient. In addition, the second stimulation therapy may be referred to as functional electrical stimulation because the second electrical stimulation therapy results in a movement of muscles of the patient that provides a specific functional result. For example, the second stimulation therapy may generate a contraction of the urinary or anal sphincter of a patient. The second stimulation therapy may also be referred to as "boost" therapy because of the additional "boost" of therapy compared to the first stimulation therapy provided by the second electrical stimulation. In examples described herein, the second stimulation therapy is delivered to the patient in a closed loop manner because the initiation of the delivery of the second stimulation therapy is dependent upon an occurrence of a trigger event, as described in further detail below.

In some examples, an implantable medical device (IMD) delivers the first and second stimulation according to different sets of stimulation parameters and/or to different target tissue sites within the patient. However, in some examples, the first and second stimulation therapies are delivered to the same nerve (e.g., the sacral or pudendal nerve).

In some examples, the IMD may deliver the first stimulation therapy to a sacral nerve to improve pelvic floor muscle tone or to an afferent fiber of the sacral or pudendal nerves to inhibit bladder contractions, e.g., to relax the bladder. In addition, in some examples, the first stimulation therapy helps close or maintain internal urinary sphincter closure or urethral tone. The IMD may deliver the second stimulation therapy to a hypogastric nerve, a pudendal nerve, a dorsal penile nerve in a male patient, a dorsal clitoral nerve in a female patient, or to the external urinary sphincter or any combination thereof to promote contraction of the internal urinary sphincter, or promote external urinary sphincter closure or periurethral muscle contraction. In some examples, the second stimulation therapy may be viewed as a short-term boost to the effectiveness of the first stimulation therapy.

The second stimulation therapy may be triggered when a patient condition indicative of an imminent involuntary voiding event or an increase in a possibility that the involuntary voiding event will occur is detected. The patient condition may be, for example, a bladder contraction. The bladder contraction may be detected via any suitable sensing mechanism or under the control of the patient. For example, the IMD may detect bladder contraction based on bladder impedance, bladder pressure, pudendal or sacral afferent nerve signals, external urinary sphincter or anal sphincter electromyogram (EMG), motion sensor signals (e.g., accelerometer signals), or any combination thereof. Instead of or in addition to a bladder contraction, the patient condition may be an abnormal detrusor muscle activity.

In other examples, the trigger event for activating the delivery of the second stimulation therapy may be patient input. In some examples described herein, the patient may use a medical device programmer or another input mechanism to trigger the IMD to deliver the second stimulation therapy. In some examples, the patient may also use the programmer to manually abort the delivery of the second stimulation therapy. In such examples, the IMD may wirelessly communicate with the programmer to alert that patient of prospective delivery of the second electrical stimulation. In additional examples, the patient may use the programmer to inhibit second electrical stimulation therapy during voluntary voiding events.

Although the techniques are primarily described in this disclosure for managing urinary incontinence, the techniques may also be applied to manage fecal incontinence. In fecal incontinence examples, the IMD delivers the second stimulation therapy when patient input is received, when a patient parameter indicative of an imminent fecal incontinence event is detected or when a patient parameter indicative of an increased probability of an occurrence of a fecal incontinence event is detected (e.g., an increased patient activity level). The patient parameter may include, for example, contraction of the anal sphincter, patient activity level or patient posture state. The IMD may use any suitable sensing mechanism to detect contraction of the anal sphincter, such as a pressure sensor or an EMG sensor.

FIG. 1 is a conceptual diagram illustrating an example therapy system 10 that delivers a first electrical stimulation therapy to generate a first physiological response of patient 14 to manage a urinary continence disorder of patient 14, and, when triggered, a second electrical stimulation therapy to generate a second physiological response of patient 14. The delivery of the second stimulation therapy provides improved protection against the occurrence of involuntary voiding events. Therapy system 10 provides the first and second therapies to generate respective physiological responses in the form of electrical stimulation. In other examples, therapy system 10 may be configured to provide at least one of the first or second therapies to mange urinary incontinence by delivering a therapeutic agent to patient 14.

Therapy system 10 includes an implantable medical device (IMD) 16, which is coupled to leads 18, 20, and 28, sensor 22, and external programmer 24. IMD 16 generally operates as a therapy device that delivers electrical stimulation to, for example, a pelvic floor nerve, a pelvic floor muscle, the urinary sphincter, the anal sphincter, or other pelvic floor targets. Pelvic floor nerves include peripheral nerves such as sacral nerves, pudendal nerves and associated branches, and dorsal genital nerves. IMD 16 provides electrical stimulation therapy to patient 14 by generating and delivering a programmable electrical stimulation signal (e.g., in the form of electrical pulses) to a target therapy site by lead 28 and, more particularly, via electrodes 29A-29D (collectively referred to as "electrodes 29") disposed proximate to a distal end of lead 28.

IMD 16 delivers the first stimulation therapy periodically over an extended period of time, e.g., chronic stimulation, and automatically delivers the second stimulation therapy within that period of time and in response to a trigger event. The second stimulation therapy is delivered for a predetermined duration of time, referred to herein as a therapy period. In other examples, IMD 16 delivers the second stimulation therapy for a period of time controlled by the patient. The first and second stimulation therapies may be delivered at substantially the same time, during overlapping time slots, or in different time slots, such that IMD 16 only delivers one type of stimulation therapy at a time. In examples in which IMD 16 delivers one type of stimulation therapy at a time, IMD 16 may deliver the first stimulation therapy, and, when triggered, deactivate delivery of the first stimulation therapy and activate delivery of the second stimulation therapy. After the second stimulation therapy period, IMD 16 may revert back to delivering the first stimulation therapy until another trigger event for activating the delivery of the second stimulation therapy is detected.

A trigger event for activating the delivery of the second stimulation therapy may be detected based on sensor or patient input. As one example, IMD 16 may sense a bladder contraction that triggers IMD 16 to deliver the second stimulation therapy. As another example, patient 14 may use external programmer 24 to provide input that causes IMD 16 to deliver the second stimulation therapy. In this way, patient 14 may control delivery of the second stimulation therapy.

IMD 16 delivers a first stimulation therapy and a second stimulation therapy to patient 14 to generate different physiological responses. For example, the first stimulation therapy may generate an afferent response by the patient, whereas the second stimulation therapy generates an efferent response. In some examples, IMD 16 delivers the first stimulation therapy to a sacral nerve of patient 14 to generate an afferent response that relaxes bladder 12, e.g., by minimizing bladder contractions. In some examples, the delivery of the first stimulation therapy by IMD 16 results in the closure or maintains the closure of internal urinary sphincter 13 at the neck of bladder 12.

In addition, in some examples, IMD 16 delivers the second stimulation therapy to promote contraction of the internal urinary sphincter 13 and external urinary sphincter 11 or periurethral muscles (not shown). In some cases, it is undesirable for the external urinary sphincter or periurethral muscles to always remain closed, i.e., during the delivery of the chronic, first stimulation therapy. However, sphincter closure may help prevent the involuntary leakage of urine from bladder 12. Thus, the short-term closure of sphincter provided by the second stimulation therapy may help prevent the occurrence of involuntary voiding events during the occurrence of acute bladder contractions. In the example shown in FIG. 1, IMD 16 generates and delivers a first stimulation therapy and a second stimulation therapy to patient 14 according to different sets of stimulation parameters.

In the example of FIG. 1, IMD 16 delivers both the first and second stimulation therapies to patient 14 via electrodes 29 on lead 28. The target therapy site for the first and second stimulation therapies may be the same in some examples, such as the different fibers of the same nerve. In other examples, the target stimulation site for the first and second stimulation therapies may be different. For example, IMD 16 may deliver the first stimulation therapy to a sacral nerve of patient 14 to relax bladder 12 and deliver the second stimulation therapy to a hypogastric nerve to contract the internal urinary sphincter and external urinary sphincter or periurethral muscles, a pudendal nerve, a dorsal penile nerve in a male patient or a dorsal clitoral nerve in a female patient to contract the external urinary sphincter, periurethral muscles, the internal urinary sphincter, or any combination thereof. In other examples, IMD 16 may deliver the first stimulation therapy to a hypogastric nerve of patient 14 to close or maintain internal urinary sphincter closure or urethral tone.

IMD 16 may be surgically implanted in patient 14 at any suitable location within patient 14, such as near the pelvis. The implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via a respective lead extension. Electrical conductors disposed within the lead bodies of leads 18, 20, and 28 electrically connect sense electrodes (not shown) and stimulation electrodes, such as electrodes 29, to a therapy delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may decrease as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired pelvic nerve or muscle site, i.e., one of the previously listed target therapy sites such as a sacral or pudendal nerve. For example, lead 28 may be positioned such that electrodes 29 deliver a first type of stimulation therapy to a sacral or pudendal nerve to relax bladder 12 and deliver the second type of stimulation therapy to hypogastric nerve, a pudendal nerve, a dorsal penile/clitoral nerve, the urinary sphincter, or any combination thereof to a promote closure of a urinary sphincter of patient 14. In FIG. 1, leads 18 and 20 are placed proximate to an exterior surface of the wall of bladder 12 at first and second locations, respectively. Electrodes 29 of the common lead 28 may deliver stimulation to the same or different nerves. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes or partial ring electrodes. Segmented and partial ring electrodes each extend along an arc less than 360 degrees (e.g., 90-120 degrees) around the outer perimeter of the respective lead 18, 20, 28. In examples, one or more of leads 18, 20, 28 may be, at least in part, paddle-shaped (i.e., a "paddle" lead). In some examples, segmented electrodes 29 of lead 28 may be useful for targeting different fibers of the same or different nerves to generate different physiological effects for the first and second stimulation therapies. As described in further detail below, segmented electrodes may be useful for delivering relatively high frequency stimulation (e.g., about 66 Hertz) and relatively low frequency stimulation (e.g., about 15 Hertz) to activate both fast twitch muscles and low twitch muscles substantially simultaneously or at alternating time slots.

In some examples, one or more of electrodes 19, 20, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of the first and/or second stimulation therapies. An electrical field represents the areas of a patient anatomical region that will be covered by an electrical field during delivery of stimulation therapy to tissue within patient 14. The electrical field may define the volume of tissue that is affected when the electrodes 19, 20, 29 are activated. An activation field represents the neurons that will be activated by the electrical field in the neural tissue proximate to the activated electrodes.

In some cases, patient 14 may perceive the delivery of the second stimulation therapy because of the increased intensity (e.g., increased amplitude and/or frequency) compared to the first stimulation therapy. The increased intensity of the second stimulation therapy may result in a change in an electrical field and/or activation field that is generated via the stimulation therapy compared to the delivery of the first stimulation therapy. Delivering the first and/or second stimulation therapies via cuff and/or segmented electrodes to achieve a more uniform electrical field or activation field distribution may help decrease changes in the intensity of therapy delivery perceived by patient 14.

The illustrated numbers and configurations of leads 18, 20, and 28 and electrodes carried by leads 18, 20, and 28 are merely exemplary. Other configurations, i.e., number and position of leads and electrodes are possible. For example, in other examples, IMD 16 may be coupled to additional leads or lead segments having one or more electrodes positioned at different locations in the pelvic region of patient 14. The additional leads may be used for delivering first or second stimulation therapies to respective stimulation sites within patient 14 or for monitoring physiological parameters of patient 14. As an example, in an example in which the target therapy sites for the first and second stimulation therapies are different, IMD 16 may be coupled to two or more leads, e.g., for bilateral or multi-lateral stimulation.

As previously indicated, IMD 16 generates and delivers a first electrical stimulation therapy to a patient to generate a first physiological effect to manage urinary or fecal incontinence and, when triggered, a second electrical stimulation therapy to provide an additional boost of therapy that generates a second physiological effect to help further manage urinary or fecal incontinence. IMD 16 controls the delivery of the second electrical stimulation therapy based on input received from patient 14 or a sensor that generates a signal indicative of a parameter of patient 14 relating to urinary incontinence, e.g., relating to a bladder condition, or fecal incontinence. As one example, IMD 16 may deliver the second stimulation therapy in response to detecting bladder contraction based on bladder impedance, bladder pressure, pudendal or sacral afferent nerve signals, a urinary sphincter EMG, or any combination thereof. As another example, IMD 16 may deliver the second stimulation therapy in response to detecting a patient activity level or patient posture state, with a sensor, which is indicative of an increased probability of an occurrence of an involuntary voiding event.

In some examples, IMD 16 may deliver the second stimulation therapy in response to receiving patient input. In this way, patient 14 may use external programmer 24 to trigger IMD 16 to deliver the second stimulation therapy.

Patient 14 may initiate the delivery of the second stimulation therapy for many reasons. In some cases, patient 14 may be afflicted with urge incontinence, and upon perceiving an urge to void, patient 14 may provide input that causes IMD 16 to deliver the second stimulation therapy. The second stimulation therapy provides an additional "boost" of stimulation that helps prevent the leakage of urine from bladder 12, e.g., by contracting internal urinary sphincter 13 and the external urinary sphincter 11. In this way, therapy system 10 provides patient 14 with direct control of the incontinence therapy.

IMD 16 delivers both the first and second stimulation therapies via electrodes 29 on lead 28. In the example shown in FIG. 1, IMD delivers the second stimulation therapy to generate the second physiological response when contraction of bladder 12 exceeding a particular threshold is detected. In the illustrated example of FIG. 1, IMD 16 determines an impedance through bladder 12, which varies as a function of the contraction of bladder 12, via electrodes 19 and 21 on leads 18 and 20, respectively. In the example shown in FIG. 1, IMD 16 determines bladder impedance using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine bladder impedance based on the transmitted electrical signal.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In the example of FIG. 1, IMD 16 also includes a sensor 22 for detecting changes in the contraction of bladder 12. Sensor 22 may be, for example, a pressure sensor for detecting changes in bladder pressure, electrodes for sensing pudendal or sacral afferent nerve signals, or electrodes for sensing urinary sphincter EMG signals (or anal sphincter EMG signals in examples in which therapy system 10 provides therapy to manage fecal incontinence), or any combination thereof. In examples in which sensor 22 is a pressure sensor, the pressure sensor may be a remote sensor that wireless transmits signals to IMD 16 or may be carried on one of leads 18, 20, or 28 or an additional lead coupled to IMD 16. In examples in which sensor 22 is one or more electrodes for sensing afferent nerve signals, the sense electrodes may be carried on one of leads 18, 20, or 28 or an additional lead coupled to IMD 16. In examples in which sensor 22 is one or more sense electrodes for generating a urinary sphincter EMG, the sense electrodes may be carried on one of leads 18, 20, or 28 or additional leads coupled to IMD 16. In any case, IMD 16 may deliver control the timing of the delivery of the second stimulation therapy based on input received from sensor 22.

In other examples, sensor 22 may comprise a patient motion sensor that generates a signal indicative of patient activity level or posture state. In some examples, IMD 16 controls the delivery of the second stimulation therapy to patient 14 upon detecting a patient activity level exceeding a particular threshold based on the signal from the motion sensor. The patient activity level that is greater than or equal to a threshold (which may be stored in a memory of IMD 16) may indicate that there is an increase in the probability that an incontinence event will occur, and, therefore, the additional boost of stimulation therapy provided by the second stimulation therapy is desirable. In this way, the second stimulation therapy provided by IMD 16 and the second physiological effect provided by the second stimulation therapy (e.g., the contraction of external urinary sphincter 11) may be useful for reacting to the circumstances that may affect patient incontinence and provide an additional layer of therapy to help prevent the occurrence of an involuntary voiding event.

In other examples, IMD 16 controls the delivery of the second stimulation therapy to patient 14 upon detecting a posture state associated with a high probability of an occurrence of an incontinence event based on the signal from the motion sensor. For example, patient 14 may be more prone to an incontinence event when patient 14 is in an upright posture state compared to a lying down posture state. IMD 16 may, for example, store a plurality of motion sensor signals and associate the signals with particular patient posture states using any suitable technique. IMD 16 may flag some of the posture states as being posture states for which additional therapy to help prevent the occurrence of an incontinence event is desirable.

System 10 may also include an external programmer 24, as shown in FIG. 1. In some examples, programmer 24 may be a wearable communication device, with boost function (e.g., activation of the second stimulation therapy) integrated into a key fob or a wrist watch, handheld computing device, computer workstation, or networked computing device. Programmer 24 may include a user interface that receives input from a user (e.g., patient 14, a patient caretaker or a clinician). The user interface may include, for example, a dedicated "boost button" to receive and confirm therapy delivery according to the second stimulation therapy, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

Patient 14 may interact with programmer 24 to control IMD 16 to deliver the second stimulation therapy, to manually abort the delivery of the second stimulation therapy by IMD 16 while IMD 16 is delivery the therapy or is about to deliver the therapy, or to inhibit the delivery of the second stimulation therapy by IMD 16, e.g., during voluntary voiding events. Patient 14 may, for example, use a keypad or touch screen of programmer 24 to cause IMD 16 to deliver the second stimulation therapy, such as when patient 14 senses that a leaking episode may be imminent. In this way, patient 14 may use programmer 24 to control the delivery of the second stimulation therapy "on demand," e.g., when an extra boost of the stimulation therapy is desirable.

In some examples, patient 14 may interact with IMD 16 (e.g., via programmer 24 or directly via IMD 16) to control IMD 16 to deliver the second stimulation therapy, manually abort the delivery of the second stimulation therapy, or inhibit the delivery of the second stimulation therapy. In such examples, a motion sensor can be integrated into or on a housing of IMD 16, whereby the motion sensor generates a signal that is indicative of patient 14 tapping IMD 16 through the skin. The number, rate, or pattern of taps may be associated with the different programming capabilities, and IMD 16 may identify the tapping by patient 14 to determine when patient input is received. In this way, patient 14 may be able to directly control delivery of therapy in the event that programmer 24 is not within reach of patient 14.

In some examples, programmer 24 may provide a notification to patient 14 when the second stimulation therapy is being delivered or notify patient 14 of the prospective delivery of the second stimulation therapy to allow patient 14 to manually abort the second stimulation therapy. In such examples, programmer 24 may display a visible message, emit an audible alert signal or provide a somatosensory alert (e.g., by controlling a housing of programmer 24 to vibrate). After generating the notification, programmer 24 may wait for input from patient 14 prior to delivering the second stimulation therapy. Patient 14 may enter input that either confirms delivery of the second stimulation therapy is permitted or desirable, or manually aborts the prospective delivery of the second stimulation therapy. In the event that no input is received within a particular range of time, programmer 24 may wirelessly transmit a signal that indicates the absence of patient input to IMD 16. IMD 16 may then elect to deliver or not to deliver the second stimulation therapy based on the programming of IMD 16.

Patient 14 may also interact with programmer 24 to inhibit the delivery of the second stimulation therapy during voluntary voiding events. That is, patient 14 may use programmer 24 to enter input that indicates the patient will be voiding voluntarily. When IMD 16 receives the input from programmer 24, IMD 16 may suspend delivery the second stimulation therapy for a predetermined period of time, e.g., two minutes, to allow the patient to voluntarily void.

A user, such as a physician, technician, surgeon, electrophysiologist, or other clinician, may also interact with programmer 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16. For example, the user may use a programmer to retrieve information from IMD 16 regarding the contraction of bladder 12 and voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 does not deliver the second stimulation therapy to patient 14 on a predetermined, scheduled basis, but as needed. For example, IMD 16 can deliver the second stimulation therapy to patient 14 when a particular patient parameter (e.g., a physiological parameter, activity level or posture state) indicative of a high probability of an occurrence of an involuntary voiding event is detected or when patient input is received. In some examples, either IMD 16 or programmer 24 may track when IMD 16 delivers the second stimulation therapy to patient 14. Frequent delivery of the second stimulation therapy may be undesirable because, for example, muscle fatigue may result. Frequent delivery of the second stimulation therapy may indicate that, as another example, bladder 12 is full.

In some examples, programmer 24 may provide a notification to patient 14 when the second stimulation therapy is triggered too frequently. The notification may be triggered based on any suitable criteria, which may be determined by a clinician or automatically programmed into IMD 16 or programmer 24. For example, in the event that the second stimulation therapy is triggered five times within five minutes, programmer 24 may provide a notification to patient 14 indicating the same. This may allow patient 14 to proceed to a bathroom before a leaking episode occurs. The notification provided by programmer 24 may also direct patient 14 to voluntarily void.

Figure 2:
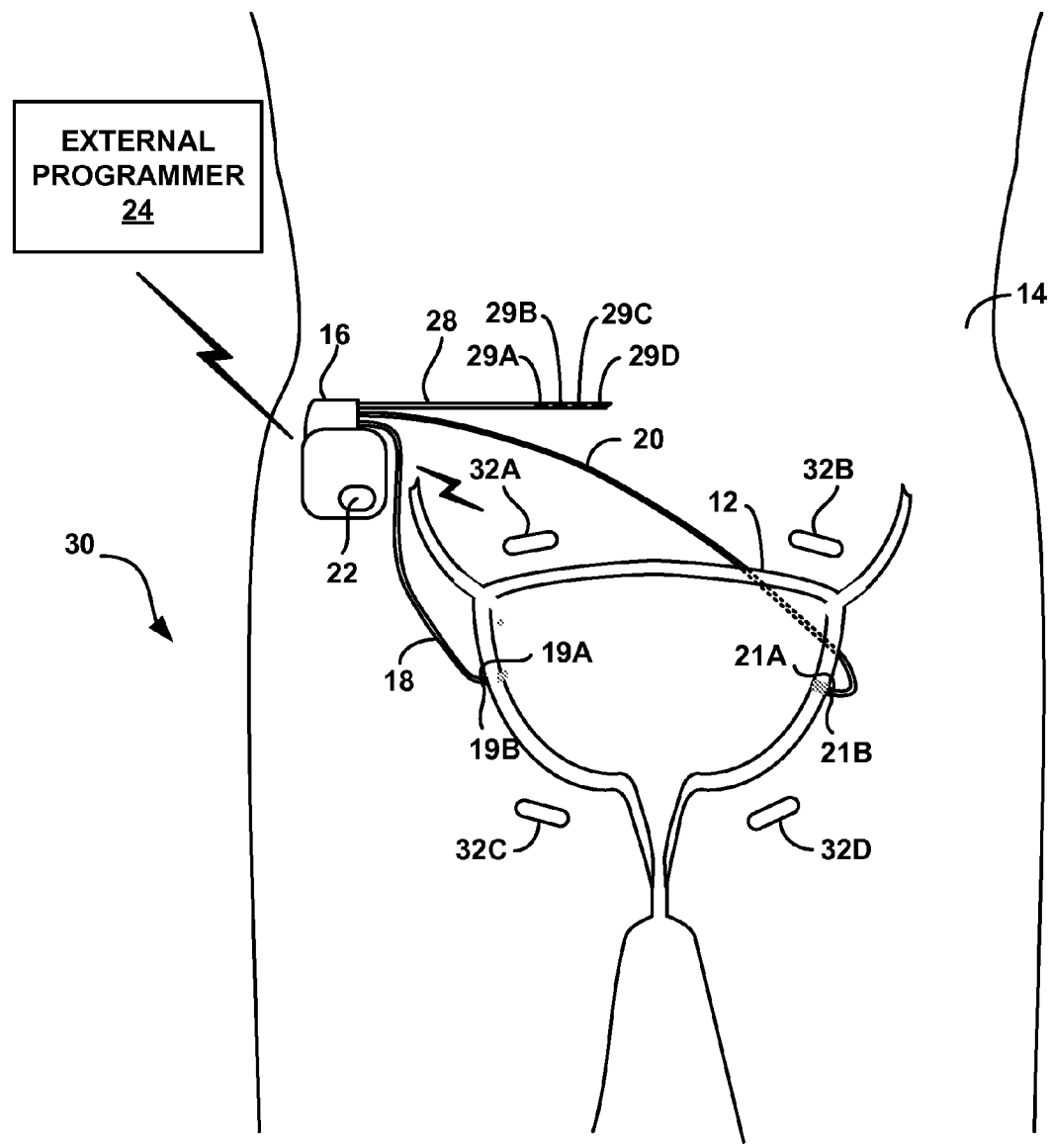
FIG. 2 is a conceptual diagram illustrating another example therapy system that delivers a first stimulation therapy and, when triggered, a second stimulation therapy to a patient to manage urinary incontinence.

FIG. 2 is conceptual diagram illustrating another example therapy system 30 that delivers a first stimulation therapy to provide a first physiological response to manage a urinary incontinence condition of patient 14, and a second stimulation therapy to provide a second, different physiological response to manage the urinary incontinence condition of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 via one or more electrodes. Microstimulators 32 have a smaller size than IMD 16, and are typically leadless.

IMD 16 may deliver one or both of the first or second electrical stimulation therapies to patient 14 via microstimulators 32. For example, IMD 16 may communicate wirelessly with microstimulators 32 via wireless telemetry to control delivery of the first and/or second stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, i.e., number and position of microstimulators, are possible.

Systems 10 and 30 shown in FIGS. 1 and 2, respectively, are merely examples of therapy systems that may provide a first stimulation therapy to provide a first physiological response to manage urinary or fecal incontinence, and a second stimulation therapy to provide a second, different physiological response to complement and "boost" the first stimulation therapy. Systems with other configurations of leads, electrodes, and sensors are possible. Additionally, in other examples, a system may include more than one IMD. For example, a system may include an IMD coupled to one or more leads for delivering the first stimulation therapy and another IMD coupled to one or more leads for delivering the second stimulation therapy.

Figure 3:
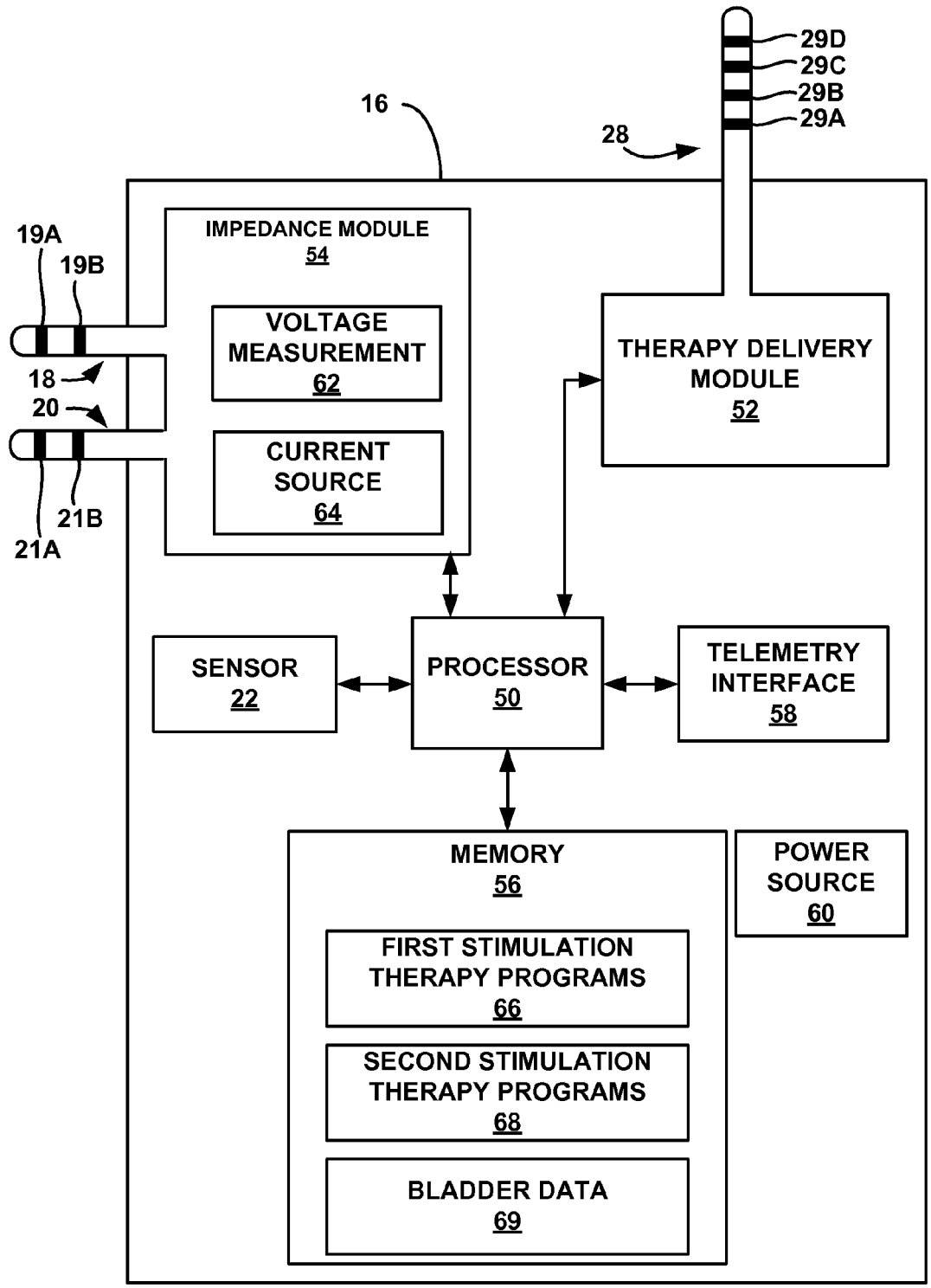
FIG. 3 is a block diagram illustrating an example configuration of the implantable medical device (IMD) of the systems shown in FIGS. 1 and 2.

FIG. 3 is a block diagram illustrating example components of IMD 16. In the example of FIG. 3, IMD 16 includes sensor 22, processor 50, therapy delivery module 52, impedance module 54, memory 56, telemetry module 58, and power source 60. Memory 56 stores first stimulation therapy programs 66 and second stimulation therapy programs 68 that specify stimulation parameters for the first and second stimulation therapies, respectively. Memory 56 also stores bladder data 69, which processor 50 may use for controlling the timing of the delivery of the second stimulation therapy. For example, bladder data 69 may include threshold values for one or more of bladder impedance, bladder pressure, sacral or pudendal afferent nerve signals, and external urinary sphincter or anal sphincter EMG templates.

Generally, therapy delivery module 52 generates and delivers therapy under the control of processor 50. In particular, processor 50 controls therapy delivery module 52 by accessing memory 56 to selectively accessing and loading first and second stimulation therapy programs 66, 68 to therapy delivery module 52. For example, in operation, processor 50 may access memory 56 to load one of first stimulation therapy programs 66 to therapy delivery module 52 and, when triggered, access memory 56 to load one of the second stimulation therapy programs 68 to therapy delivery module 52. Consistent with the techniques described in this disclosure, processor 50 may load one of second stimulation therapy programs 68 to therapy delivery module 52 based on input received from impedance module 54, sensor 22, or an indication of patient input received from another device and transmitted to IMD 16 via telemetry module 58.

By way of example, processor 50 may access memory 56 to load one of first stimulation therapy programs 66 to therapy module 52 for delivering the first stimulation therapy to patient 14. A clinician or patient 14 may select a particular one of first stimulation therapy programs 66 from a list using a programming device, such as programmer 24 or a clinician programmer. Processor 50 may receive the selection via telemetry module 58. Therapy delivery module 52 delivers the first stimulation therapy to patient 14 according to the selected program for an extended period of time, such as hours, days, weeks, or until patient 14 or a clinician manually stops or changes the program. The first stimulation therapy program 66 may define a schedule or an "on cycle" and "off cycle" duration for the first stimulation therapy, such that a stimulation signal is not continuously delivered to patient 14, but periodically delivered in accordance with predetermined parameters for the first stimulation therapy.

Upon detecting a condition in which the second stimulation therapy is desirable to help prevent the occurrence of an incontinence event, such as in response to detecting bladder contractions or receiving patient input, processor 50 accesses memory 56 to load one of second stimulation therapy programs 68 to therapy delivery module 52. Therapy delivery module 52 delivers the second stimulation therapy according to the selected program. In some examples, therapy module 52 delivers the second stimulation therapy for a predetermined therapy period, the duration of which may be stored in memory 56. The therapy period may be, for example, approximately 10 seconds to approximately 50 seconds, although other therapy periods are contemplated. That is, therapy delivery module 52 may deliver therapy according to second stimulation therapy programs 68 via bursts of stimulation for a duration of approximately 10 seconds to approximately 60 seconds and subsequently reverts to delivering therapy according to one of first stimulation therapy programs 66.

In some examples, therapy module 52 delivers the second stimulation therapy for a period of time controlled by the patient. In such examples, the patient may interact with programmer 24 to control the delivery time. As an example, IMD 16 may deliver the second stimulation therapy as long as the patient presses a "boost" button on a keypad or touch screen of programmer 24. In operation, processor 50 receives the patient input via telemetry module 58 and controls therapy delivery module 52 to deliver therapy according to the received input.

In other examples, such as examples in which IMD 16 delivers the second stimulation therapy based on a sensed patient condition, therapy module 52 delivers the second stimulation therapy until the condition is no longer detected. For example, IMD 16 may deliver the second stimulation therapy in response to detecting a bladder impedance greater than or equal to a predetermined threshold and continue delivering the second stimulation therapy until the bladder impedance is less than the predetermined threshold. If the second stimulation therapy is delivered for more than one consecutive therapy, IMD 16 may separate the consecutive therapy periods by at least a predetermined minimum inter-therapy interval. In some examples, the minimum inter-therapy interval is about 10 seconds, although other intervals are contemplated.

In some examples, IMD 16 delivers the second stimulation therapy at substantially the same time as the first stimulation therapy, such that the first and second physiological effects from the first and second stimulation therapy, respectively, overlap. In other examples, the first and second stimulation therapies are not delivered at the same time, such that IMD 16 only delivers one type of therapy at a time. The alternating therapies may be implemented if, for example, IMD 16 delivers the first and second stimulation therapies with a common set of electrodes. In the latter technique, when the second stimulation therapy has been delivered, IMD 16 may revert back to delivering the first stimulation therapy according to a first stimulation therapy program 66 selected from memory 56.

Therapy module 52 delivers therapy, i.e., electrical stimulation, according to stimulation parameters, such as voltage or current amplitude, pulse rate (frequency), and pulse width specified by therapy programs, such as first stimulation therapy programs 66 and second stimulation therapy programs 68. In some examples, therapy delivery module 52 delivers therapy in the form of electrical pulses. In other examples, therapy delivery module 52 delivers electrical stimulation in the form of continuous waveforms.

In some examples, the stimulation parameters for the first stimulation programs 66 may be selected to relax bladder 12 (FIG. 1) or close or maintain internal urinary sphincter closure or urethral tone. An example range of stimulation parameters for the first stimulation therapy that are likely to be effective in treating incontinence, e.g., when applied to the sacral or pudendal nerves, are as follows:

1. Frequency: between approximately 0.5 Hz and approximately 500 Hz, such as between approximately 10 Hz and approximately 250 Hz, or between approximately 10 Hz and approximately 25 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds (µs) and approximately 5000 µs, such as between approximately 100 µs and approximately 1000 µs, or between approximately 180 µs and approximately 450 µs.

The stimulation parameters for second stimulation therapy programs 68 are generally different than those for first stimulation therapy programs 66. Stimulation parameters for second stimulation therapy programs 68 may be selected to maximize closure of one or more of internal urinary sphincter, external urinary sphincter, and periurethral muscles. Stimulation parameters for second stimulation therapy programs 68 may also be selected to minimize muscle fatigue. Muscle fatigue may occur when the force-generating ability of a muscle decreases as a result of the electrical stimulation.

An example range of stimulation pulse parameters for the second stimulation therapy are as follows:

1. Frequency: between approximately 15 Hz to approximately 30 Hz to activate slow-twitch muscles to minimize muscle fatigue while providing some sphincter closure, and between approximately 30 Hz and approximately 66 Hz to activate fast-twitch muscles, which may maximize sphincter closure.

2. Amplitude: approximately 2-8 times rheobase (e.g., approximately 2-4 times rheobase) for the target nerve or muscle (e.g., the sphincter muscle), such as about 0.5 volts to about 50 volts, or about 0.5 volts to about 10 volts, or about 4 volts to about 8 volts. Rheobase is the minimal electric current of infinite duration that results in an action potential or muscle twitch.

3. Pulse Width: between about 10 microseconds (µs) and about 5,000 µs, such as between about 100 µs and approximately 1,000 µs.

As previously indicated, IMD 16 may deliver the second stimulation therapy for duration of time referred to as a therapy period. In some examples, the therapy period has a duration of about 10 seconds to about 50 seconds, although other therapy period durations are contemplated. In some examples, the therapy period duration is controlled by patient 14 through programmer 24, and may have a maximum period limit of about 3 minutes, although other maximum therapy periods for the second stimulation therapy is contemplated.

At least one of second stimulation therapy programs 68 may include more than one set of stimulation parameters. In such examples, one set of stimulation parameters may be designed to activate fast-twitch muscle fibers in order to maximize closure of the urinary sphincter and/or periurethral muscles, and another set of stimulation parameters may be designed to activate slow-twitch muscle fibers in order to maintain closure of the urinary sphincter and/or periurethral muscles while minimizing muscle fatigue. The fast-twitch and slow-twitch muscle fibers may be selectively activated by activating specific nerve fibers with the same electrodes of a common lead, or different electrodes of a common lead (e.g., segmented electrodes specifically selected to target particular nerve fibers) or electrodes of separate leads or microstimulators.

As an example, in accordance with one of the second stimulation therapy programs 68, IMD 16 may generate and deliver stimulation pulses having a relatively high frequency (e.g., about 66 Hz) for the first five seconds of the therapy interval to activate fast-twitch muscle fibers, and subsequently generate and deliver stimulation pulses at a lower relative frequency (e.g., 30 Hz) for the following 10 seconds to activate slow-twitch muscle fibers. An example stimulation signal that IMD 16 may generate and deliver as part of the second stimulation therapy is described with respect to in FIG. 11.

In some examples, the portion of the second stimulation therapy that activates the fast twitch muscles is delivered for a shorter duration of time than the portion of the second stimulation therapy that activates the slow twitch muscles. This may help minimize muscle fatigue by providing the fast twitch muscles with a longer recovery time. It has been found that some fast twitch muscles require a longer time to recover, e.g., to regain contraction force, following the delivery of stimulation, than slow twitch muscles. Muscles may be recovered when the contraction force under stimulation is close or substantially equal to the contraction force under the same stimulation intensity while there is no fatigue e.g., when the muscles are stimulated a first time after a relatively long time of rest in which no stimulation was delivered. If the muscle is stimulated again with the same therapy parameter values, and the contraction force is the same, then the muscle may be considered to have recovered from the previous delivery of stimulation.

In some examples, processor 50 may control the timing of the second stimulation therapy relative to the first stimulation therapy in a manner that minimizes muscle fatigue. For example, processor 50 may utilize an inter-therapy interval to prevent the second stimulation therapy from being delivered so frequently that the pelvic muscles fatigue and render second stimulation therapy less effective or even ineffective. The inter-therapy interval is a predetermined amount of time, e.g., 10 seconds, following a delivery of a therapy period of the second stimulation therapy during which IMD 16 cannot deliver a subsequent therapy period of the second stimulation therapy. In this way, in some examples, the second stimulation therapy cannot be triggered within a minimal inter-therapy interval following previously delivered second stimulation therapy to prevent muscle fatigue. Thus, if the second stimulation therapy is triggered within the inter-therapy interval (e.g., based on a sensed patient parameter or patient input) processor 50 of IMD 16 may control therapy delivery module 52 to generate and deliver the second stimulation therapy only after the inter-therapy interval has lapsed. Alternatively, processor 50 may ignore sensor input (e.g., input from impedance module 54) or patient input received via telemetry module 58 for the duration of the inter-therapy interval. An example of the application of the inter-therapy interval is provided in FIG. 12.

In some examples, processor 50 may adjust a second stimulation therapy program 68 for one or more consecutive therapy periods to configure the second stimulation therapy to minimize muscle fatigue. In this way, IMD 16 may provide second stimulation therapy that is delivered in an adaptive fashion. In some examples, processor 50 may implement an inter-therapy interval, but rather than abstaining from delivery of the second stimulation therapy when the second stimulation therapy is triggered within an inter-therapy interval, processor 50 controls therapy delivery module 52 to generate and deliver stimulation according to an adjusted second stimulation therapy.

As one example, if second stimulation therapy is triggered within the inter-therapy interval following the delivery of a previous second stimulation therapy, the adaptive stimulation program may decrease the duration of fast-twitch muscle stimulation defined by the previously-implemented second stimulation therapy program by a first time increment (e.g., five seconds) and increase the duration of slow-twitch muscle stimulation by the same or different time increment. As another example, for each second stimulation therapy triggered within an inter-therapy interval, the adaptive stimulation program may replace the first five second of fast-twitch muscle stimulation by five second of slow-twitch muscle stimulation compared to the previously delivered the second stimulation therapy signal. Example adaptive stimulation signals that may be delivered as part of the second stimulation therapy are described below with respect to FIGS. 13A-13C and 14A-14C.

In other examples, second stimulation therapy programs 68 may define the simultaneous delivery of stimulation at multiple frequencies. As an example, a stored second stimulation therapy program 68 may define segmented electrodes to simultaneously deliver higher frequency (e.g., 66 Hz) stimulation to fascicles responsible for fast muscles, such as the Iliococcygeus muscle and the pubococcygeus muscle, and lower frequency stimulation (e.g., 30 Hz) to fascicles responsible for slow muscles, such as the soleus muscle.

In the example of FIG. 3, therapy delivery module 52 drives a single lead 28. Specifically, therapy delivery module 52 delivers electrical stimulation to tissue of patient 14 via selected electrodes 29A-29D carried by lead 28. A proximal end of lead 28 extends from the housing of IMD 16 and a distal end of lead 28 extends to target therapy sites within the pelvic floor, such as tissue sites proximate a sacral nerve, a pudendal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as an axial leads with ring electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16. In yet other examples, such as system 30 shown in FIG. 2 that includes microstimulators 32, processor 50 may act as a "master" module that controls microstimulators to deliver stimulation at target therapy sites. In other examples, however, one of microstimulators 32 may act as a master module or microstimulators 32 may be self-controlled.

In some examples, processor 50 controls therapy module 52 to deliver the second stimulation therapy to patient 14 based on signals received from impedance module 54, sensor 22, or patient input received via telemetry module 58. In the example shown in FIG. 3, processor 50 monitors bladder impedance to detect bladder contraction based on signals received from impedance module 54. For example, processor 50 may determine an impedance value based on signals received from impedance module 54 and compare the determined impedance value to a threshold impedance value stored in memory 56 as bladder data 69. When the determined impedance value is less than the threshold value stored in bladder data 69, processor 50 detects bladder contraction and loads one of second stimulation therapy programs 68 in therapy module 52, and therapy module 52 generates and delivers the second stimulation therapy to patient 14 to generate a physiological response that helps prevent an incontinence event. As previously indicated, the physiological response generated by the delivery of the second stimulation therapy differs from the physiological response generated by the delivery of the first stimulation therapy to provide an additional layer of incontinence prevention.

In the example of FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, processor 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Processor 50 determines an impedance value from the measure voltage values received from voltage measurement circuitry 52.

As previously described, sensor 22 may be a pressure sensor for detecting changes in bladder pressure, electrodes for sensing pudendal or sacral afferent nerve signals, or electrodes for sensing external urinary sphincter EMG signals (or anal sphincter signals in examples in which IMD 16 provides fecal incontinence therapy), or any combination thereof. Alternatively, sensor 22 may be a motion sensor, such as a two-axis accelerometer, three-axis accelerometer, one or more gyroscopes, pressure transducers, piezoelectric crystals, or other sensors that generate a signal that changes as patient activity level or posture state changes. Processor 50 may detect a patient condition indicative of a high probability of an incontinence event (e.g., bladder contraction or abnormal detrusor muscle activity) or other trigger events based on signals received from sensor 22 in addition to instead of impedance module 54. Sensor 22 may also be a motion sensor that is responsive to tapping (e.g., by patient 14) on skin superior to IMD 16 and, as previously described, processor 50 may control therapy module 52 to deliver second stimulation therapy, manually abort delivery of second stimulation therapy, or inhibit the delivery of second stimulation therapy, in response to detection of the patient tapping.

One type of bladder contraction detection algorithm indicates an occurrence of a bladder contraction for which delivery of the second stimulation therapy is desirable upon sensing of a signal that exhibits a certain characteristic, which may be a time domain characteristic (e.g., an amplitude) or a frequency domain characteristic (e.g., an energy level in one or more frequency bands). For example, the bladder contraction detection algorithm may indicate the occurrence of a bladder contraction for which delivery of the second stimulation therapy is desirable when the amplitude of the signal from sensor 22 meets a certain condition relative to a threshold (e.g., is greater than, equal to or less than the threshold). Another bladder contraction detection algorithm indicates the occurrence of a bladder contraction for which delivery of the second stimulation therapy is desirable if a sensed signal substantially correlates to a signal template, e.g., in terms of frequency, amplitude and/or spectral energy characteristics. IMD 16 may use known techniques to correlate a sensed signal with a template in order to detect the bladder contraction or detect the bladder contraction based on the frequency domain characteristics of a sensed signal. Other bladder contraction techniques may be used.

In examples in which sensor 22 includes a pressure sensor, processor 50 may determine a pressure value based on signals received from the pressure sensor and compare the determined pressure value to a threshold value stored in bladder data 69 to determine whether the contractions of bladder 12 are indicative of an imminent incontinence event. In examples in which sensor 22 includes an EMG sensor, processor 50 may generate an EMG from the received signals generated by sensor 22 (e.g., which may sense the muscle activity with one or more sensor positioned near the target muscle) and compare the EMG to templates stored as bladder data to determine whether the contractions of bladder 12 are indicative of an imminent incontinence event. Alternatively, processor 50 may compare previously collected EMGs to a current EMG to detect changes over time. The techniques for detecting bladder contractions may also be applied to detecting abnormal detrusor muscle activities.

As described above, in examples in which processor 50 monitors a patient condition indicative of bladder contraction, processor 50 may control therapy delivery module 52 to generate and deliver the second stimulation therapy to generate the second physiological response only if the bladder contraction is greater than a threshold level. The threshold level may indicate a bladder contraction intensity (e.g., strength or frequency) that is indicative of an imminent involuntary voiding event or a relatively high probably an involuntary voiding event will occur. In some cases, the bladder contraction may be indicative of a voluntary voiding event. Thus, in some examples, processor 50 can control therapy delivery module 52 to generate and deliver the second stimulation therapy if the bladder contraction is greater than first threshold level, but less than a second threshold level.

In examples in which sensor 22 includes a motion sensor, processor 50 may determine a patient activity level or posture state based on a signal generated by sensor 22. For example, processor 50 may determine a patient activity level by sampling the signal from sensor 22 and determining a number of activity counts during a sample period, where a plurality of activity levels are associated with respective activity counts. In one example, processor 50 compares the signal generated by sensor 22 to one or more amplitude thresholds stored within memory 56, and identifies each threshold crossing as an activity count.

Processor 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, processor 50 indicates that patient 14 is in the posture state associated with the predefined space.

Memory 56 may associate patient posture states or activity levels with the second stimulation therapy, such that when processor 50 detects a posture state or activity level associated with the second stimulation therapy, processor 50 controls therapy delivery module 52 to generate and deliver the second stimulation therapy to patient 14. Certain posture states or activity levels may be associated with a higher incidence of incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of the second stimulation therapy.

The threshold values (also referred to as threshold levels) or templates (e.g., indicating a signal indicative of an imminent voiding event) stored in memory 56 as bladder data 69 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on user input, e.g., via external programmer 24. As an example, patient 14 may indicate, via programmer 24, when an involuntary voiding event takes place. When the patient input is received, processor 50 may determine an impedance value during the event or immediately prior to the event based in signals received from impedance module 54. A new threshold value may be determined using this impedance value. For example, the threshold value stored as bladder data 69 may be a running average of impedance values measured during involuntary voiding events.

In some examples, IMD 16 includes impedance sensing module 54 and not sensor 22, while in other examples, IMD 16 includes sensor 22, but not impedance sensing module 54. Moreover, in some examples, sensor 22 and/or impedance sensing module 54 may be physically separate from IMD 16. Physically separate sensors may be useful in examples in which either sensor 22 and/or impedance sensing module 54 sense one or more physiological parameters at a location that is not accessible by IMD 16 or difficult to access by IMD 16.

Processor 50 may control therapy delivery module 52 to deliver the second stimulation therapy based on patient input received via telemetry module 58. Telemetry module 58 includes any suitable hardware, firmware, software or any combination thereof for communicating with another device, such as programmer 24 (FIG. 1). Under the control of processor 50, telemetry module 58 may receive downlink telemetry, e.g., patient input, from and send uplink telemetry, e.g., an alert, to programmer 24 with the aid of an antenna, which may be internal and/or external. Processor 50 may provide the data to be uplinked to programmer 24 and the control signals for the telemetry circuit within telemetry module 58, and receive data from telemetry module 58.

Generally, processor 50 controls telemetry module 58 to exchange information with medical device programmer 24. Processor 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

As previously described, telemetry module 58 may receive an indication that patient 14 provided input indicative of an imminent voiding event or a desire for delivery of the "boost" of stimulation, e.g., the second stimulation therapy, from programmer 24. Upon receiving the patient input via telemetry module 58, processor 50 may control therapy delivery module 52 to generate and deliver the second stimulation therapy for a predetermined amount of time or until a particular patient condition is detected, to manually abort the second stimulation therapy, or inhibit the second stimulation therapy during voluntary voiding. Processor 50 monitors patient input received via telemetry module 58 and takes appropriate action. For example, telemetry module 58 may receive input from programmer 24 that indicates a specified one of second stimulation therapy programs 68 should be selected for delivery of the second stimulation therapy program. Upon receiving the input, processor 50 loads the specified one of second stimulation therapy programs 68 to therapy module 52.

In an example in which telemetry module 58 receives patient input that indicates the second stimulation therapy should be aborted, processor 50 may transmit a signal to programmer 24 via telemetry module 58 to notify patient 14 of the prospective delivery of the second stimulation therapy. The notification may be provided, for example, within less than a minute (e.g., a few seconds) prior to the delivery of the second stimulation therapy. This notification provides patient 14 with the opportunity to intervene if the second stimulation therapy is not deemed necessary by patient 14 or if patient 14 is voluntarily voiding and the second stimulation therapy may hinder the voluntary voiding attempt. Processor 50 may control therapy module 52 to revert back to delivering the first stimulation therapy if the patient manually aborts the delivery of the second stimulation therapy.

Upon receiving the notification of the prospective delivery of the second stimulation therapy, patient 14 may also provide active input that indicates IMD 16 can deliver the second stimulation therapy or patient 14 may merely not intervene to indicate IMD 16 should deliver the second stimulation therapy. Upon receiving the input confirming the second stimulation therapy or lack of input aborting the second stimulation therapy, processor 50 may load one of first stimulation therapy programs 66 to therapy module 52.

In an example in which telemetry module 58 receives patient input indicating a voluntary voiding event, processor 50 may suspend delivery of the second stimulation therapy for a pre-determined period of time, e.g., 2 minutes. In response to receiving the input, processor 50 may ignore signals indicative of the patient parameter, such as impedance signals received from impedance module 54. Processor 50 may ignore these signals for a predetermined period of time, such as approximately two minutes. After two minutes has elapse, processor 50 may continue monitoring patient 14 to detect trigger events.

The processors described in this disclosure, such as processor 50 and processing circuitry in impedance module 54 and other modules, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. In some examples, the processing circuitry of impedance module 54 that determines an impedance based on a measured voltage and/or current of a signal may be the same microprocessor, ASIC, DSP, or other digital logic circuitry that forms at least part of processor 50.

Memory 56 may also store instructions for execution by processor 50, in addition to first and second stimulation therapy programs 66, 68, and bladder data 69. Information related to measured impedance and determined posture may be recorded for long-term storage and retrieval by a user, or used by processor 50 for adjustment of stimulation parameters, such as amplitude, pulse width, and pulse rate. Memory 56 may include separate memories for storing instructions, electrical signal information, stimulation programs, and bladder data.

Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 56 may store program instructions that, when executed by processor 50, cause IMD 16 to perform the functions ascribed to IMD 16 herein.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
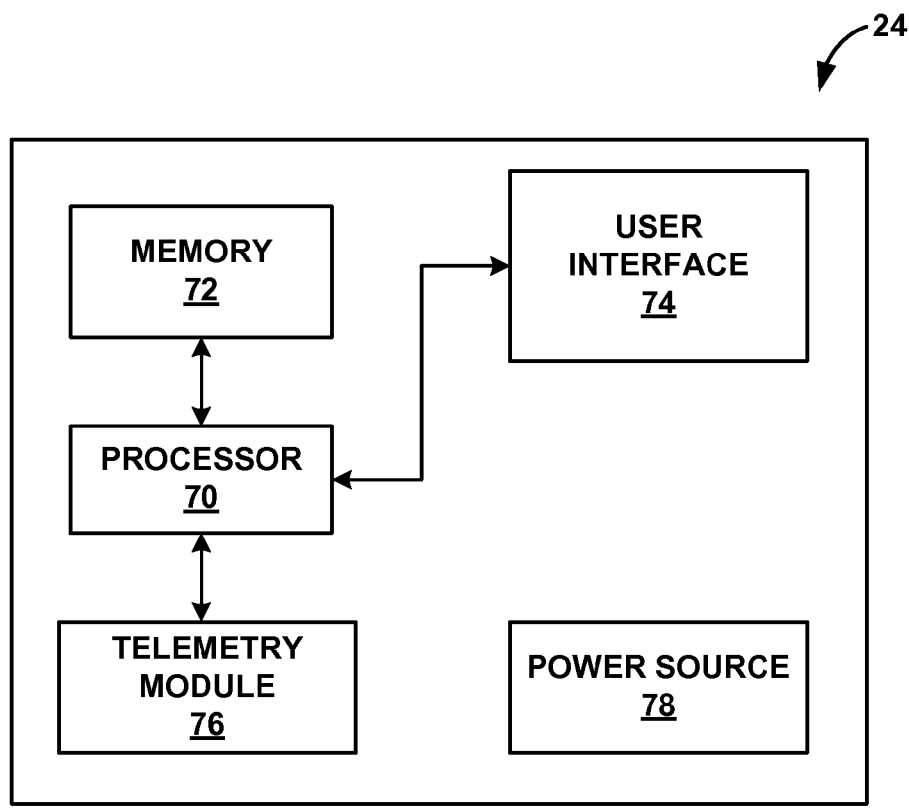
FIG. 4 is a block diagram illustrating an example configuration of the external programmer of the systems shown in FIGS. 1 and 2.

FIG. 4 is a block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 70, memory 72, user interface 74, telemetry module 76, and power source 78. Memory 72 may store program instructions that, when executed by processor 70, cause processor 70 and external programmer 24 to provide the functionality ascribed to external programmer 24 throughout this disclosure.

In some examples, memory 72 may further include program information, i.e., therapy programs defining the first type of stimulation therapy and therapy programs defining the second type of stimulation therapy similar to those stored in memory 56 of IMD 16. The stimulation programs stored in memory 72 may be downloaded into memory 56 of IMD 16. Memory 72 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 70 can take the form one or more microprocessors, DSPs, ASICs, FPGAs, programmable logic circuitry, or the like, and the functions attributed to processor 70 herein may be embodied as hardware, firmware, software or any combination thereof.

User interface 74 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 70 may present and receive information relating to stimulation therapy via user interface 74. For example, processor 70 may receive patient input via user interface 74. The input may be, for example, in the form of pressing a button on a keypad or selecting an icon from a touch screen.

Processor 70 may also present information to the patient in the form of alerts related to delivery of the second stimulation therapy to patient 14 or a caregiver, as will be described in more detail below, via user interface 74.

Although not shown, external programmer 24 may additionally or alternatively include a data or network interface to another computing device, to facilitate communication with the other device, and presentation of information relating to first and second stimulation therapies via the other device.

Telemetry module 78 supports wireless communication between IMD 16 and external programmer 24 under the control of processor 70. Telemetry module 78 may also be configured to communicate with another computing device via wireless communication techniques, or direct communication through a wired connection. Telemetry module 78 may be substantially similar to telemetry module 58 described above, providing wireless communication via an RF or proximal inductive medium. In some examples, telemetry module 78 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the first and second stimulation therapies that generate different physiological responses to manage urinary or fecal incontinence. If external programmer 24 controls the stimulation, programmer 24 may transmit therapy programs for implementation by IMD 16 to IMD 16 via telemetry module 78. A user (e.g., patient 14 or a clinician) may select the first and second stimulation therapy programs from a list provided via a display of user interface 74. Alternatively, external programmer 24 may transmit a signal to IMD 16 indicating that IMD 16 should execute locally stored programs or therapy routines. In such a manner, control over the electrical stimulation may be distributed between IMD 16 and external programmer 24, or may reside in either one alone.

In one example, patient 14 may control the stimulation therapy delivered by IMD 16 via external programmer 24. For example, patient 14 may initiate or terminate delivery of either the first or second stimulation therapies by IMD 16 via external programmer 24. For example, patient 14 may selectively control the delivery of the second stimulation therapy by IMD 16 through input entered via user interface 74. That is, IMD 16 may deliver second stimulation therapy based on patient input entered via user interface 74. In this way, patient 14 may use programmer 24 to deliver the second stimulation therapy "on demand," such as when patient 14 senses the onset of a leakage episode.

In another example, programmer 24 may present a notification indicative of the prospective delivery of the second stimulation therapy to patient 14 via user interface 74. As an example, prior to delivering the second stimulation therapy, processor 70 of programmer 24 may generate and present a notification that indicates the second stimulation therapy will be delivered within an indicated period of time. IMD 16 may provide an indication to programmer 24 via the respective telemetry modules 58, 76 that IMD 16 intends on delivering the second stimulation therapy. Programmer 24 may alert patient 14 by presenting a warning message on a display of user interface 74, emitting an audible alert, or generating a somatosensory alert (e.g., a vibrating housing). In such an example, programmer 24 may prompt patient 14 for input via a display of user interface 74. Patient 14 may enter input via user interface 74 that either confirms delivery of the second stimulation therapy or input for manually aborting the second stimulation therapy. In either case, the patient input is transmitted to IMD 16 via telemetry module 78.

As previously indicated, programmer 24 may provide a notification to patient 14 when the second stimulation therapy is triggered too frequently, which may indicate that bladder 12 (FIG. 1) is full. Processor 70 may implement any suitable criteria to generate the alert. Processor 70 may monitor the frequency of the delivery of the second stimulation therapy by IMD 16, e.g., by receiving input from IMD 16 indicating the times at which the second stimulation therapy is delivered to patient 14 or based on patient input received via user interface 74, where the patient input controls the delivery of the second stimulation therapy. For example, in the event that the second stimulation therapy is triggered five times within five minutes, processor 50 may generate a notification to patient 14 indicating the same. This may allow patient 14 to proceed to a bathroom before a leaking episode occurs. The notification provided by programmer 24 may also direct patient 14 to locate a restroom and voluntarily void.

Patient 14 may indicate an intent to void via user interface 74, and processor 70 may implement a blanking interval through communication of the indication to IMD 16 via telemetry module 78. For example, processor 70 may transmit a command signal to IMD 16 that indicates IMD 16 should temporarily suspend delivery of the second stimulation therapy. In some cases, this may permit voluntary voiding by patient 14. In some examples, the length of time for a voiding event may be determined by pressing and holding down a button of user interface 74 for the duration of a voiding event, pressing a button a first time to initiate voiding and a second time when voiding is complete, or based on a predetermined period of time following the indication of voluntary voiding provided by patient 14. In each case, programmer 24 causes IMD 16 to temporarily suspend the second stimulation therapy, and, in some cases, the first stimulation therapy, so that voluntary voiding is possible.

In other examples, IMD 16 may automatically determine when patient 14 is attempting to voluntary void, e.g., based on a voiding signature of an EMG signal indicative of bladder activity or based on bladder pressure or contraction. In such examples, IMD 16 may automatically suspend the delivery of either or both the first and second stimulation therapies to permit patient 14 to voluntary void. In some cases, suspension of stimulation by IMD 16 is not necessary to facilitate voiding, and stimulation may occur substantially simultaneously with the voluntary voiding. For example, the bladder volume will eventually increase to a level to trigger strong bladder contractions that prevails over the second stimulation therapy to allow voiding.

Power source 78 delivers operating power to the components of programmer 24. Power source 78 may include a battery and a power generation circuit to produce the operating power. In some examples, the battery may be rechargeable to allow extended operation. Recharging may be accomplished by electrically coupling power source 78 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 78 may include circuitry to monitor power remaining within a battery. In this manner, user interface 74 may provide a current battery level indicator or low battery level indicator when the battery needs to be replaced or recharged. In some cases, power source 78 may be capable of estimating the remaining time of operation using the current battery.

FIGS. 5-10 are flow diagrams illustrating example techniques to reduce the likelihood of incontinence events with a therapy system that generates and delivers first stimulation therapy that generates a first physiological response by patient 14 and a second stimulation therapy that generates a second physiological response. The first stimulation therapy may be delivered in as part of open loop therapy that does not use feedback from a sensor to trigger therapy delivery, while the second stimulation therapy is delivered as part of closed loop therapy that utilizes patient input or feedback from a sensor to trigger therapy delivery. The flow diagrams shown in FIGS. 5-10 include some of the same steps, which are like-numbered for ease of description. The example technique shown in FIGS. 6-10 may be viewed as specific examples of the technique shown in FIG. 5.

Figure 5:
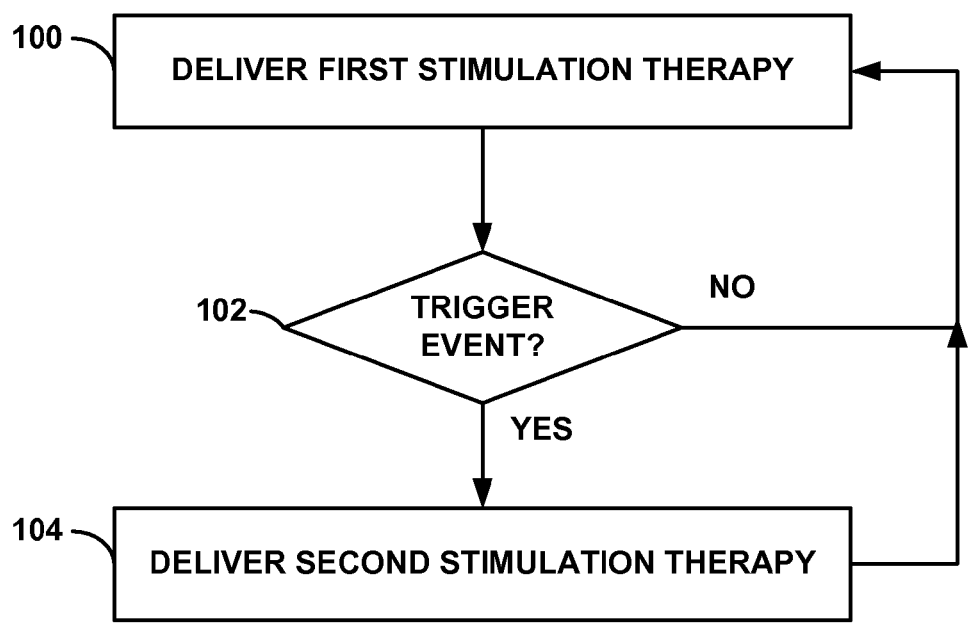
FIGS. 5-10 are flow diagrams illustrating example techniques of delivering first stimulation therapy and, when triggered, a second stimulation therapy to a patient to manage urinary incontinence.

FIG. 5 is a flow diagram illustrating an example technique for delivering first and second stimulation therapies to a patient to manage fecal or urinary incontinence. IMD 16 delivers first stimulation therapy to patient 14 (100). In some examples, IMD 16 initiates the delivery of the first stimulation therapy upon activation of chronic therapy delivery by the clinician. IMD 16 delivers the first stimulation therapy chronically, e.g., periodically for an extended period of time, such as hours, days, weeks, or, in examples in which the first and second stimulation therapies are not delivered simultaneously, until an event occurs that triggers delivery of the second stimulation therapy.

IMD 16 monitors a patient condition via a sensor to determine whether a trigger event is detected (102). Example trigger events may be detected include, but are not limited to, bladder contraction exceeding (e.g., greater than or equal to) a threshold level, abnormal detrusor muscle activities (e.g., as indicated by an EMG) patient activity level exceeding a threshold level, patient posture state, and patient input. As previously described, IMD 16 may monitor bladder impedance, bladder pressure, pudendal or sacral afferent nerve signals, a urinary sphincter EMG, or any combination there of to detect changes in bladder contraction.

The steps of delivering the first stimulation therapy and monitoring the patient to detect a trigger event are illustrated in FIG. 5 as being sequential, but it should be understood that these steps may be performed simultaneously instead of sequentially. As an example, IMD 16 may deliver the first stimulation therapy to patient 14 for an extended period of time. During the extended period of time, IMD 16 may periodically monitor patient 14 to detect a trigger event. In some examples, IMD 16 may monitor patient 14 following delivery of a train of first stimulation therapy, e.g., in examples in which the first stimulation therapy is defined by a plurality of consecutive trains of stimulation separated by intervals of time. In other examples, IMD 16 may monitor patient 14 more frequently or less frequently. In yet other examples, IMD 16 may monitor patient 14 substantially continuously.

If IMD 16 does not detect a trigger event ("NO" branch of block 102), IMD 16 continues to deliver the first stimulation therapy (100). On the other hand, if IMD 16 detects a trigger event ("YES" branch of block 102), IMD 16 delivers the second stimulation therapy (104). The first and second stimulation therapies may be delivered substantially simultaneously or in an alternating manner (e.g., one type of stimulation is delivered at a time).

In some examples, IMD 16 delivers the second stimulation therapy for a predetermined period of time, e.g., about 10 seconds to about 50 seconds. The duration of the predetermined period of time may be selected such that an imminent involuntary voiding event is suppressed. As described in further detail below with reference to FIG. 9, in some examples, after the predetermined period of time, IMD 16 determines whether the patient condition that triggered the delivery of the second stimulation therapy is still present. For example, IMD 16 may determine whether the bladder contractions are still greater than or equal to a threshold value. If the patient condition that triggered the delivery of the second stimulation therapy is still present, IMD 16 may deliver the second stimulation therapy again for another predetermined period of time.

In other examples, IMD 16 delivers the second stimulation therapy for a period of time controlled by patient 14. For example, patient 14 may control the duration of the second stimulation therapy by interacting with programmer 24, e.g., by pressing a "boost" button on a keypad or a touch screen, or by interacting directly with IMD 16 (e.g., by tapping skin superior to the implanted IMD 16). A maximum therapy period for patient controlled stimulation may be approximately 3 minutes, although other time ranges are contemplated.

After completion of the delivery of the second stimulation therapy, IMD 16 reverts back to delivering the first stimulation therapy (100) and the technique shown in FIG. 5 are repeated as necessary. Thus, IMD 16 delivers the first stimulation therapy and, when triggered, delivers the second stimulation therapy for a limited duration of time (e.g., shorter in duration than the duration of time that the first stimulation therapy is delivered). That is, IMD 16 delivers chronic stimulation for an extended period of time via the first stimulation therapy, and, when necessary or desirable, delivers an additional boost of stimulation via the second stimulation therapy. The boost of stimulation is provided for a comparatively short period of time within the extended period of time during which the chronic therapy delivery is provided.

In this way, IMD 16 provides responsive stimulation to control urinary incontinence. Delivering the second stimulation therapy upon detection of a trigger event, rather than on a substantially regular basis, may help reduce muscle fatigue by limiting the amount of the second stimulation therapy provided to patient 14. In addition, implementing the second stimulation therapy only when needed may help conserve power of power source 60 of IMD 16. Conserving power may help elongate the useful life of IMD 16.

Figure 6:
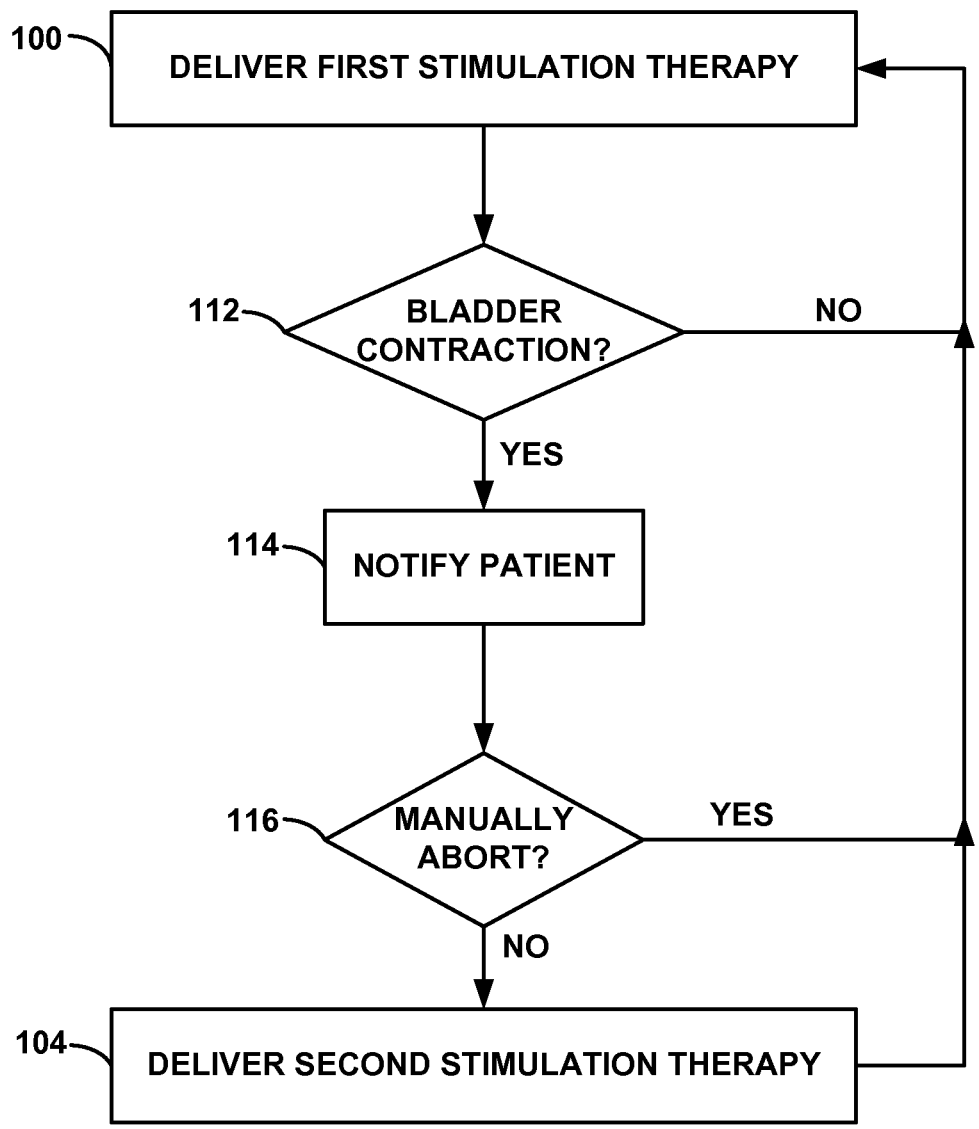

FIG. 6 is a flow diagram illustrating an example technique for delivering a first stimulation therapy to manage incontinence of patient 14 and, when triggered by sensed bladder contraction, delivering a second stimulation therapy to patient 14 to provide an additional mechanism resulting in a different physiological effect that further helps prevent an involuntary voiding event. The technique shown in FIG. 6 allows patient 14 to manually abort the delivery of the second stimulation therapy. In the description of FIG. 6, bladder contractions are referred to as the trigger event for activating the delivery of the second stimulation therapy. In other examples, the trigger event may be any suitable trigger event, such as the detection of patient input, a particular patient posture state, a patient activity level greater than threshold value, or detrusor muscle activities greater than or equal to a threshold value or substantially matching a template.

As with the technique shown in FIG. 5, processor 50 of IMD 16 controls therapy delivery module 52 to generate and deliver the first stimulation therapy to patient 14 (100). Processor 50 monitors a physiological parameter of patient 14 to detect bladder contraction (112). For example, processor 50 may monitor bladder impedance with the aid of signals generated by impedance module 54, or bladder pressure, pudendal or sacral afferent nerve signals, a urinary sphincter EMG, or any combination thereof with the aid of signals generated by sensor 22.

If processor 50 of IMD 16 does not detect bladder contractions that are greater than or equal to a threshold level ("NO" branch of block 112), IMD 16 continues to deliver the first stimulation therapy (100). On the other hand, if processor 50 determines that sensed bladder contractions are indicative of an imminent voiding event or at least an increased probability of an occurrence of an involuntary voiding event (e.g., as indicated by a bladder contraction greater than or equal to a threshold level) ("YES" branch of block 112), processor 50 generates a notification for patient 14 (114). The notification may indicate that bladder contraction indicative of an imminent involuntary voiding event has been detected. IMD 16 may alert patient 14 by, for example, wirelessly communicating with programmer 24 to cause programmer 24 to provide an alert. Programmer 24 may alert the patient by displaying a warning message within a display or emitting an alert sound. In other examples, IMD 16 may generate the patient notification by generating a somatosensory alert (e.g., by generating a notification that is felt by patient 14). For example, IMD 16 may cause an outer housing of IMD 16 to vibrate.

After notifying patient 14 (114), IMD 16 determines whether patient 14 has indicated that the second stimulation therapy should be aborted (116) prior to actually delivering the second stimulation therapy stimulation. In some examples, IMD 16 may determine if patient 14 wants to manually abort the delivery of the second stimulation therapy based on patient input. The patient input may be input entered via programmer 24. As an example, patient 14 may press a button on a keypad or select an icon using a touch screen to enter input. Programmer 24 wirelessly transmits the patient input to IMD 16. As another example, patient 14 may provide input by tapping the skin proximate IMD 16 in a predetermined pattern, such that IMD 16 detects the movement (e.g., via a signal generated by a motion sensor) and characterizes the movement as patient input.

When the patient input indicates that patient 14 wants to stop the delivery of the second stimulation therapy ("YES" branch of block 116), IMD 16 continues to deliver the first stimulation therapy (100). Patient 14 may want to abort the delivery of the second stimulation therapy, for example, during a voluntary voiding event. Permitting patient 14 to manually abort the delivery of second stimulation therapy may also allow patient 14 to prevent unwanted stimulation in the event that IMD 16 incorrectly detected the bladder contraction.

If processor 50 of IMD 16 determines that patient 14 does not want to manually abort the delivery of the second stimulation therapy ("NO" branch of block 116), IMD 16 delivers the second stimulation therapy for a therapy period, which may be predetermined (104). Processor 50 may automatically determine that patient 14 does not want to manually abort the delivery of the second stimulation therapy by receiving input from patient 14 indicating that the second stimulation therapy is desirable. In other examples, processor 50 automatically determines that patient 14 does not want to manually abort the delivery of the second stimulation therapy if patient 14 does not provide any input within a certain period of time following the patient notification. After IMD 16 delivers the second stimulation therapy for a therapy period (104), IMD 16 continues to deliver the first stimulation therapy (100).

Figure 7:
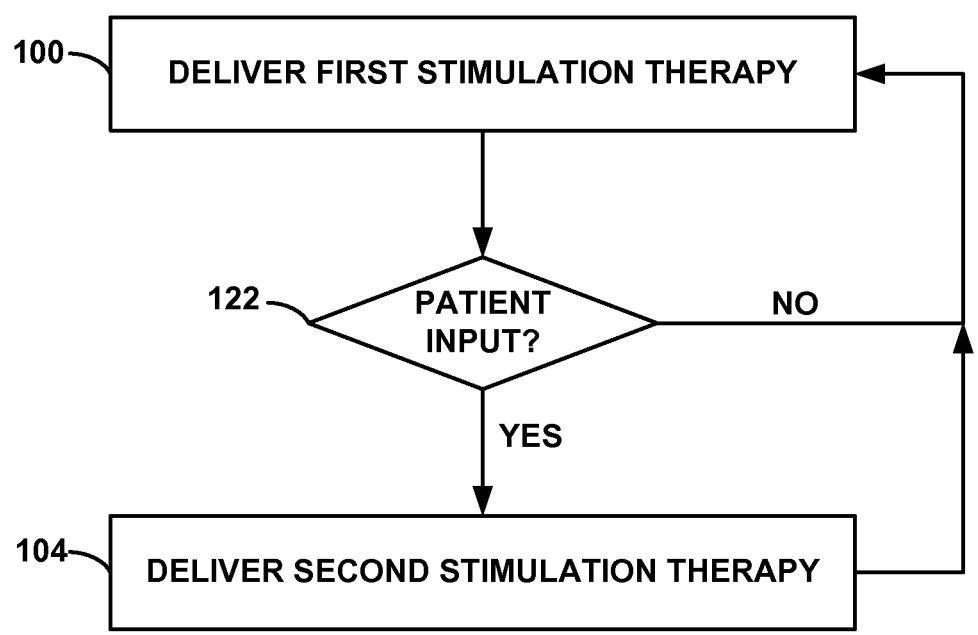

FIG. 7 is a flow diagram illustrating an example technique for delivering a stimulation therapy to patient 14 to manage urinary or fecal incontinence, where the technique includes delivering a first, primary electrical stimulation therapy and, upon receiving patient input, delivering a second stimulation therapy. The example technique shown in FIG. 7 is an example of the technique shown in FIG. 5. That is, the event that triggers the delivery of the second stimulation therapy in FIG. 7 is patient input.

In accordance with the technique shown in FIG. 7, IMD 16 delivers first stimulation therapy to patient 14 (100). Upon receiving patient input (122), processor 50 of IMD 16 controls therapy delivery module 52 to generate and deliver the second stimulation therapy to patient 14 to generate the second physiological response that helps prevent an involuntary voiding event. In some cases, processor 50 of IMD 16 upon receiving patient input to discontinue the delivery of the first stimulation therapy prior to the delivery of the second stimulation therapy, while in other examples the first and second stimulation therapies are delivered substantially simultaneously.

As previously indicated, patient 14 may provide the patient input via programmer 24, e.g., by activating a button on a keypad or select an icon using a touch screen of programmer 24. Programmer 24 wirelessly communicates the patient input to IMD 16. In other examples, patient 14 may provide input indicating the delivery of the second stimulation therapy is desirable via IMD 16. For example, IMD 16 may include a motion sensor that detects movement of IMD 16 and patient 14 may provide input by tapping the skin proximate IMD 16 in a predetermined pattern, such that IMD 16 detects the movement and characterizes the movement as patient input.

If IMD 16 does not receive patient input that activates the delivery of the second stimulation therapy ("NO" branch of block 122), IMD 16 continues to deliver the first stimulation therapy (100) and monitor for patient input.

Figure 8:
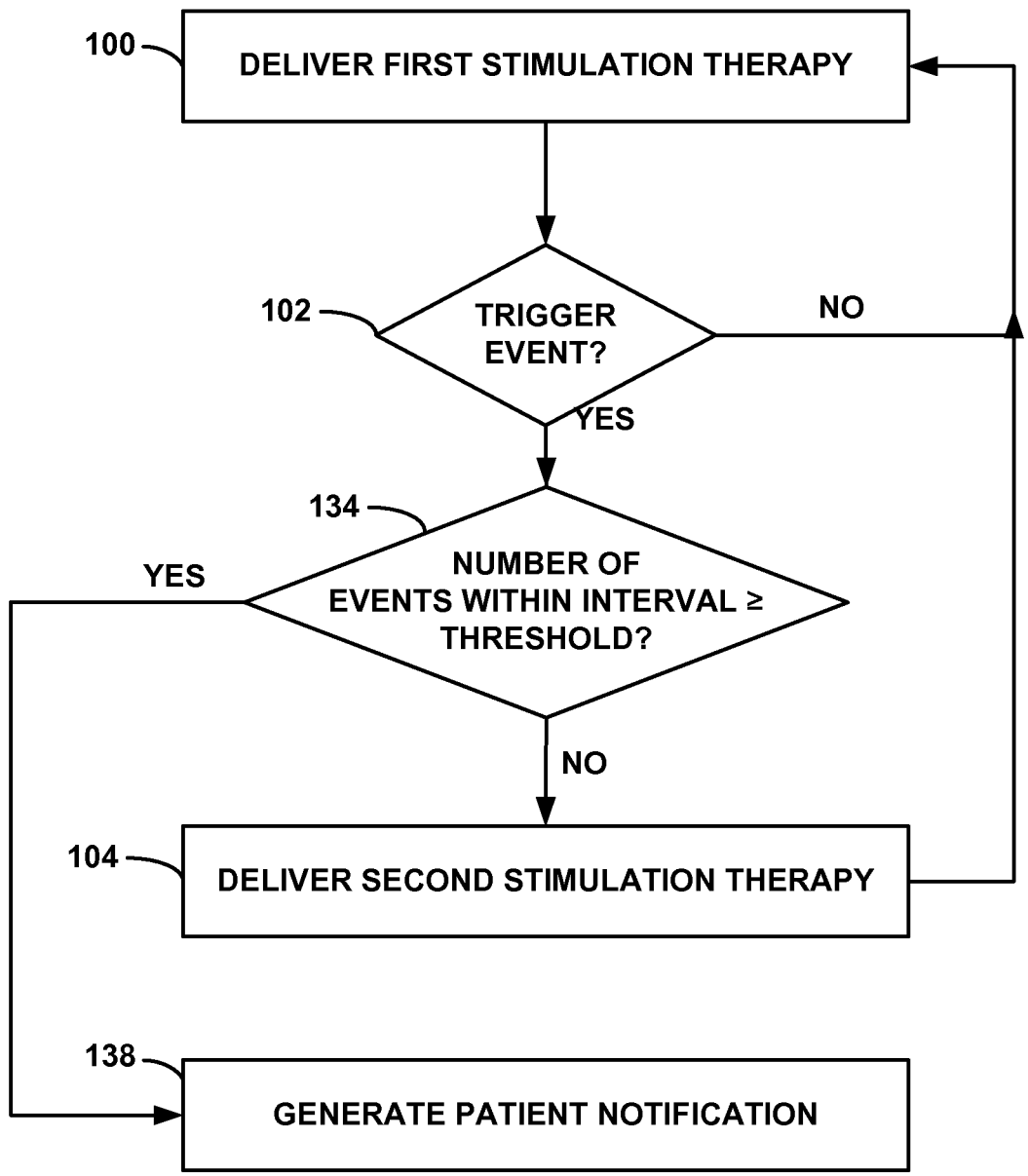

FIG. 8 is a flow diagram illustrating an example technique for controlling the delivery of the second stimulation therapy to patient 14, and notifying patient 14 when the second stimulation therapy is delivered too frequently. As with the techniques shown in FIGS. 5-7, IMD 16 first delivers a first stimulation therapy to patient 14 (100). In accordance with the previously described example methods, IMD 16 monitors a patient parameter (e.g., a physiological parameter, activity level or posture state) and/or patient input to detect a trigger event (102).

If IMD 16 does not detect a trigger event ("NO" branch of block 102), IMD 16 continues to deliver the first stimulation therapy (100). However, if IMD 16 detects a trigger event ("YES" branch of block 102), IMD 16 determines whether too many trigger events occurred within a predetermined interval (134). In the example shown in FIG. 8, processor 50 of IMD 16 compares the number of trigger events detected within the a predetermined interval to a threshold value, which may be stored in memory 56 (FIG. 3) of IMD 16.

If processor 50 determines that too many trigger events occurred within the predetermined interval of time ("YES" branch of block 134), processor 50 generates an alert to notify patient 14 that the trigger events that activate the delivery of the second stimulation therapy are occurring too frequently (138). Trigger events occurring at a frequency higher than a stored frequency may indicate that bladder 12 (FIG. 1) is full. Processor 50 (or processor 70 of programmer 24) may track the number of trigger events within the predetermined range of time using any suitable technique, such as by implementing a counter.

If processor 50 determines that too many trigger events have not occurred within the predetermined interval of time ("NO" branch of block 134), IMD 16 delivers the second stimulation therapy stimulation to patient 14 (104) and repeats the technique shown in FIG. 8 as necessary.

Figure 9:
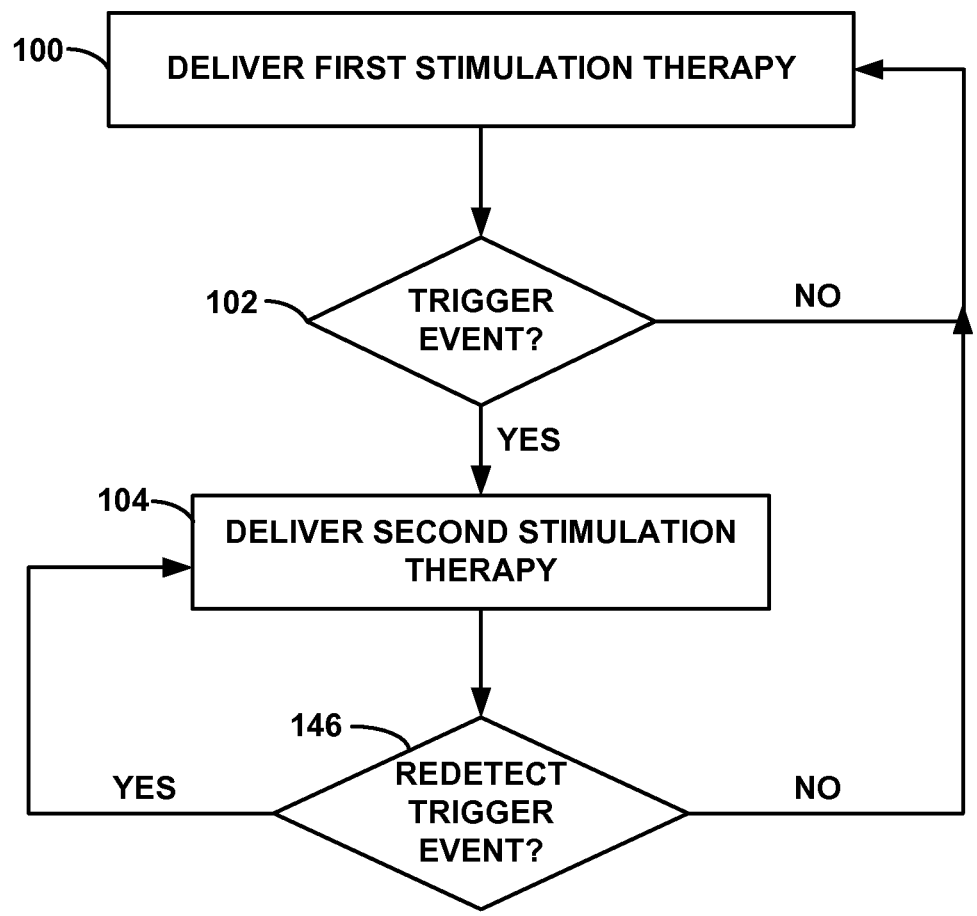

FIG. 9 is a flow diagram illustrating another example technique for delivering first stimulation therapy to manage incontinence and, when triggered by sensor or patient input, delivering a second stimulation therapy to boost the effectiveness of the first stimulation therapy. In the example technique illustrated in FIG. 9, the second stimulation therapy is delivered for another therapy period if a trigger event is still detected after the stimulation therapy was delivered for a therapy period. Each therapy period may include the delivery of stimulation signals for a predetermined duration of time. In the technique shown in FIG. 9, IMD 16 delivers the second stimulation therapy until the trigger event is no longer detected or the therapy interval is over.

IMD 16 first delivers the first stimulation therapy to patient 14 (100) and monitors patient 14 to detect a trigger event (102). If IMD 16 does not detect a trigger event ("NO" branch of block 102), IMD 16 continues deliver the first stimulation therapy (100) until a trigger event is detected. Upon detecting the trigger event ("YES" branch of block 102), IMD 16 delivers the second stimulation therapy stimulation to patient 14 (104). In the example shown in FIG. 9, IMD 16 delivers the second stimulation therapy to patient 14 by delivering a plurality of stimulation signals during a predetermined range of time, which may be referred to as a therapy period.

After delivering the second stimulation therapy for the therapy period, IMD 16 determines whether the trigger event is detected again or is still occurring (146). In an example in which the trigger event is contraction of bladder 12 of patient 14, IMD 16 determines whether the contraction of bladder 12 is greater than or equal to a threshold level. If the bladder contraction subsided during the first therapy period ("NO" branch of block 146), IMD 16 deactivates delivery of the second stimulation therapy and reverts back to delivering the first stimulation therapy (100) and monitoring the patient for another trigger event (102). On the hand, if processor 50 of IMD 16 redetects the trigger event ("YES" branch of block 146), IMD 16 continues to deliver the second stimulation therapy for a second therapy period (104).

After the second therapy period, processor 50 determines whether the trigger event is still present (146), and continues to control therapy delivery module 52 (FIG. 3) deliver the second stimulation therapy until the trigger event is no longer present. In other examples, processor 50 controls therapy delivery module 52 to deliver the second stimulation therapy until the trigger event is no longer present or until a maximum number of therapy periods have been delivered within a certain amount of time. The maximum number of therapy periods within certain amount of time may be stored in memory 56 of IMD 16 or another device, and may be selected by a clinician.

Figure 10:
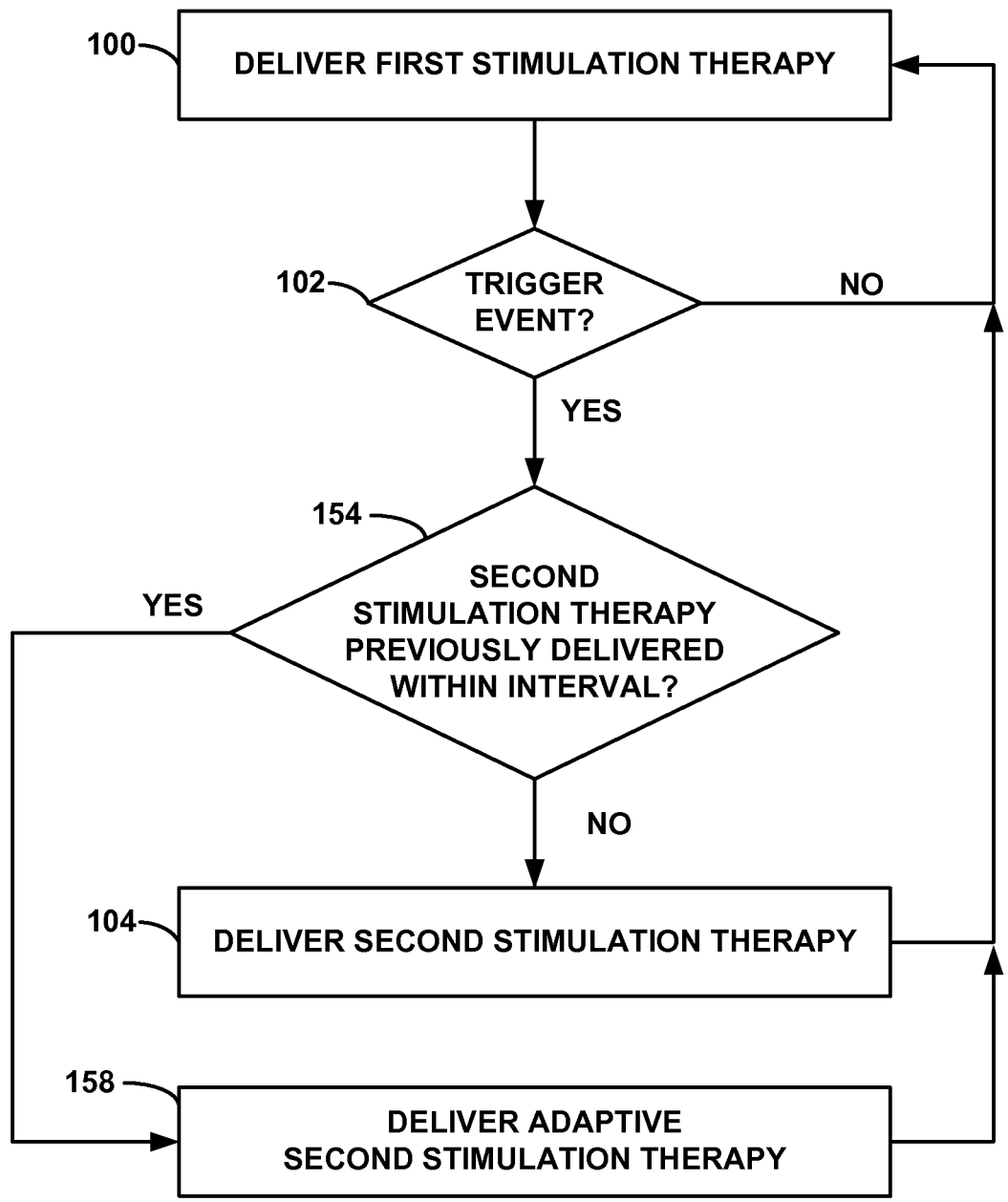

FIG. 10 is a flow diagram illustrating an example technique for delivering first stimulation therapy and, when triggered by sensor input or patient input, delivering adaptive second stimulation therapy to a patient. Adaptive second stimulation therapy includes second stimulation therapy that generates a different physiological response than the first stimulation therapy, whereby the stimulation parameters of the second stimulation therapy changes over time. Adaptive second stimulation therapy may be configured to maximize closure of the urinary or anal sphincter and minimize muscle fatigue.

IMD 16 delivers first stimulation therapy to patient 14 (100) and monitors signals from one or more sensors and/or patient input to detect trigger events (102). If processor 50 of IMD 16 does not detect a trigger event ("NO" branch of block 102), IMD 16 continues to deliver the first stimulation therapy. However, if processor 50 detects a trigger event ("YES" branch of block 102), IMD 16 determines whether the second stimulation therapy, which is a temporary "dose" of stimulation therapy, was previously delivered within a predetermined interval of time (154). The predetermined interval of time may be referred to as an inter-therapy interval and may be, for example, approximately 30 seconds, although other intervals of time are contemplated.

If IMD 16 has not previously delivered the second stimulation therapy within the interval of time ("NO" branch of block 154), IMD 16 delivers the second stimulation therapy to patient 14 without modifying the therapy parameters of the second stimulation therapy (104). On the other hand, if processor 50 of IMD 16 determines that IMD 16 has previously delivered the second stimulation therapy within the interval of time ("YES" branch of block 154), processor 50 controls therapy delivery module 52 (FIG. 3) to generate and deliver adaptive second stimulation therapy to patient 14 (158). Processor 50 adjusts one or more parameters of the second stimulation therapy if IMD 16 has previously delivered the second stimulation therapy within the interval of time, thereby providing "adaptive" second stimulation therapy. Adjusting one or more parameters of the second stimulation therapy help minimize patient adaptation to the second stimulation therapy, as well as any muscle fatigue that may result from the second stimulation therapy.

In general, changing one or more aspects of the second stimulation therapy if IMD 16 has previously delivered the second stimulation therapy within the predetermined interval of time may help prevent the same stimulation signal from being delivered to patient 14 for a relatively long period of time. This helps prevent patient 14 from growing accustomed to the stimulation signal, e.g., adaptation, which may result in a decrease in the effectiveness of the second stimulation therapy over time. In addition, changing one or more aspects of the second stimulation therapy may help reduce muscle fatigue by changing the way in which the muscles of patient 14 are stimulated by the second stimulation therapy.

IMD 16 delivers the adaptive second stimulation therapy (158) by delivering the second stimulation therapy according to different parameters than then previously delivered the second stimulation therapy. As an example, IMD 16 may deliver adaptive second stimulation therapy by delivering second stimulation therapy that stimulates fast-twitch muscles during a first therapy period, and the second stimulation therapy that stimulates slow-twitch muscles during a second therapy period subsequent to the first therapy period, and varying the duration of the first and second intervals over time each time that adaptive second stimulation therapy is delivered within the predetermined interval. Example stimulation signals that illustrate adaptive second stimulation therapy is described with respect to FIGS. 13A-14C.

While the techniques described with reference to FIGS. 6-10 are primarily described as being performed by processor 50 of IMD 16, in other examples, processor 70 of programmer 24 or a processor of another computing device may perform any part of the techniques in FIG. 5-10 or any other technique described herein. In addition, any of the techniques shown in FIGS. 5-10 for controlling the delivery of stimulation therapy to patient 14 to manage incontinence may be used in combination with each other.

Figure 11:
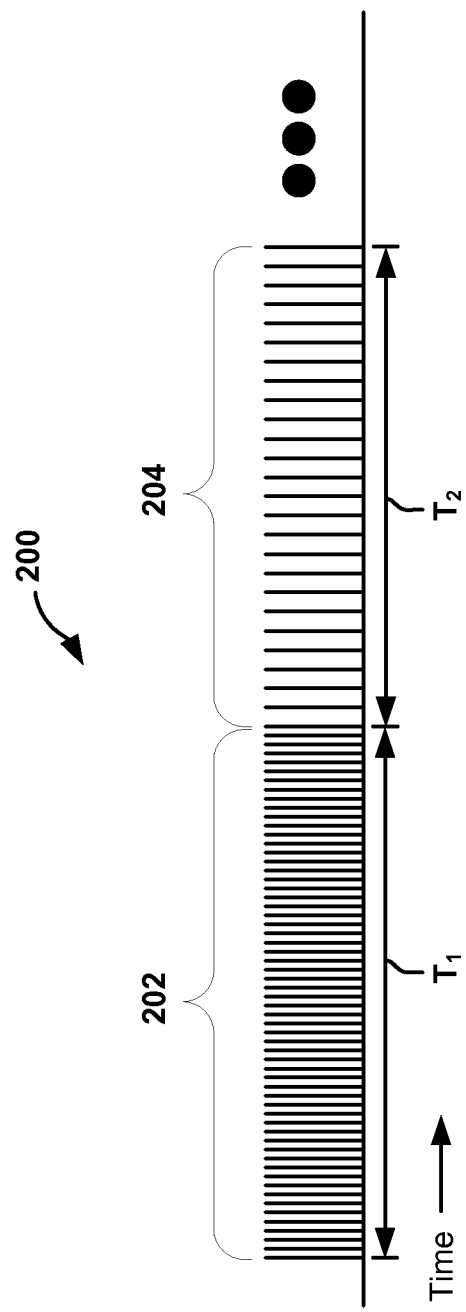
FIGS. 11, 12, 13A-13C, and 14A-14C illustrate example stimulation signals that may be delivered as part of a second stimulation therapy.

FIG. 11 illustrates an example stimulation signal 200 that therapy delivery module 52 of IMD 16 may generate and deliver as part of the second stimulation therapy. Stimulation signal 200 includes stimulation pulses 202 and stimulation pulses 204. In the example shown in FIG. 11, stimulation pulses 202 are delivered over an interval that has duration $T_1$ and stimulation pulses 204 are delivered over an interval that has duration $T_2$. Stimulation pulses 202 are delivered at a higher frequency than stimulation pulses 204. The high frequency stimulation pulses 202 may be designed to maximize closure of the urinary sphincter or bladder outlet while the low frequency stimulation pulses 204 may be designed to minimize muscle fatigue. By alternating the delivery of the high and low frequency stimulation pulses 202, 204, respectively, the second stimulation therapy may be configured to reduce muscle fatigue while minimizing the possibility of an occurrence of an involuntary voiding event.

As previously indicated, IMD 16 may deliver the second stimulation therapy for a predetermined therapy period. In some examples, during the therapy period, IMD 16 may provide the first stimulation therapy to patient 14 by delivering stimulation pulses 202 at a frequency of approximately 40 Hz to approximately 66 Hz for a duration of approximately 10 seconds to 20 seconds, and subsequently deliver stimulation pulses 204 at a frequency of approximately 30 Hz for a duration of approximately 10 seconds to approximately 20 seconds. Other stimulation parameters are contemplated.

Additionally, although the stimulation pulses of stimulation signal 200, i.e., relatively high frequency stimulation pulses 202 and relatively low stimulation pulses 204, are shown in FIG. 11 as a continuous train of pulses, stimulation pulses may also be delivered in other configurations, such as bursts of pulses. For example, one or both of stimulation pulses 202 and 204 may be delivered as bursts of pulses. The bursts of pulses may be controlled, for example, by selecting duty cycle values, e.g., approximately 50% ON/50% OFF, approximately 30% ON/70% OFF, or approximately 20% ON/80% OFF.

Figure 12:
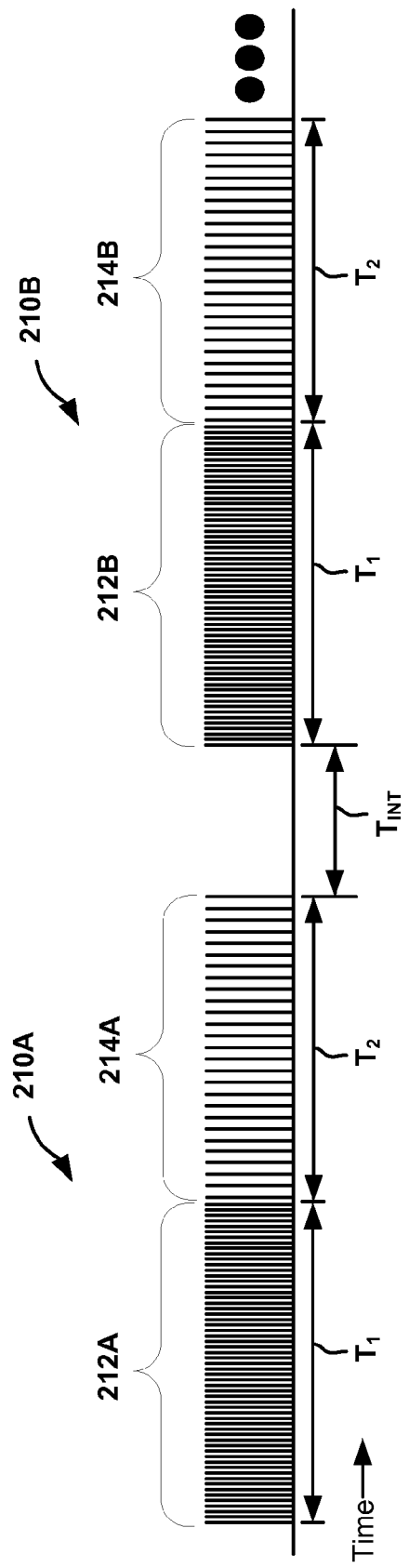
Figure 13:
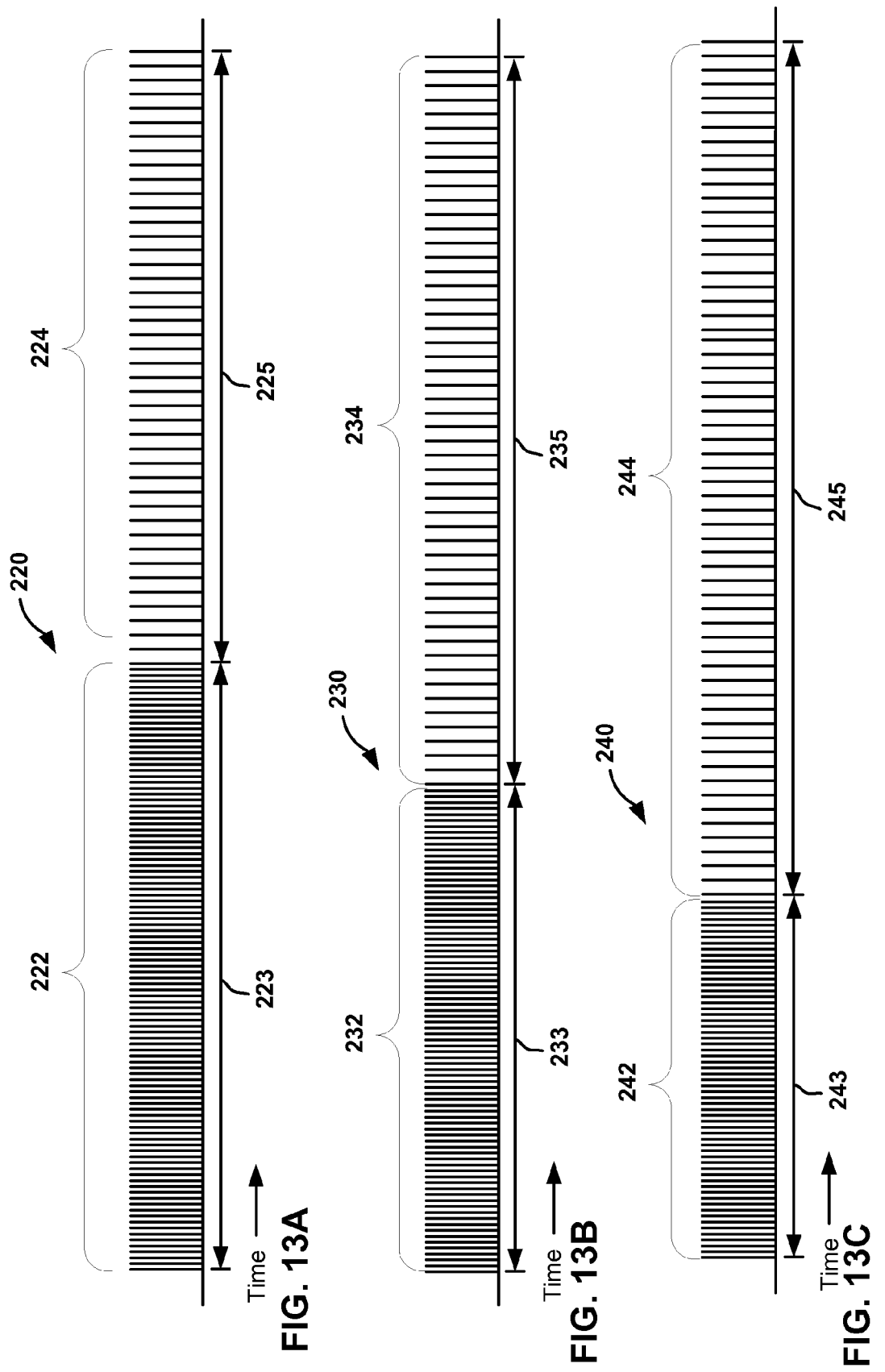
Figure 14:
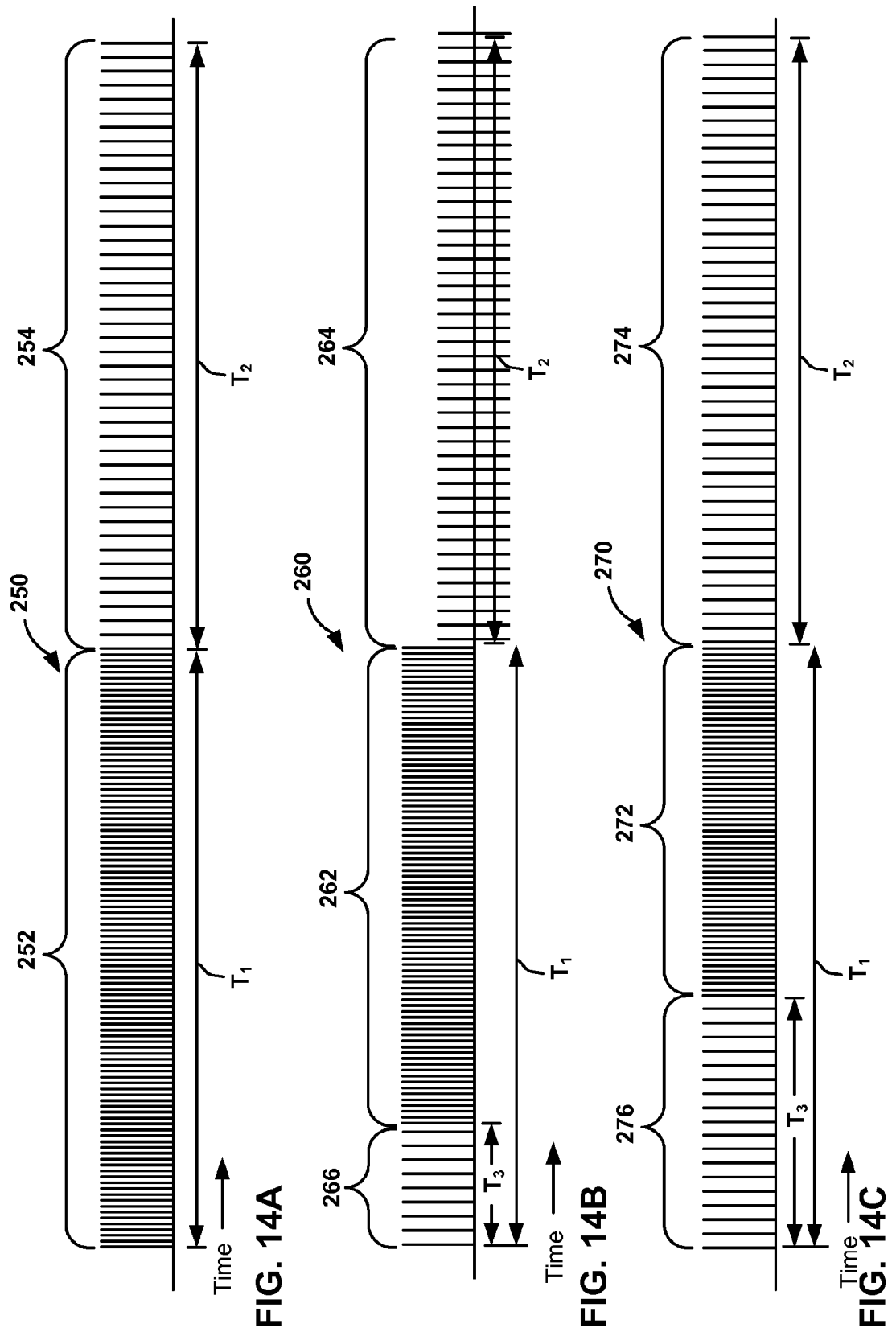

FIG. 12 illustrates example stimulation signals 210A and 210B that therapy delivery module 52 of IMD 16 may generate and deliver as part of the second stimulation therapy. Stimulation signal 210A includes bursts of relatively high frequency stimulation pulses 212A and relatively low frequency stimulation pulses 214A. Stimulation signal 210B includes bursts of relatively high frequency stimulation pulses 212B and relatively low frequency stimulation pulses 214B. In the example shown in FIG. 12, stimulation signals 210A and 210B are similar to stimulation signal 200 shown in FIG. 11 and, thus, are also similar to each other.

As shown in FIG. 12, IMD 16 does not deliver stimulation during the inter-therapy interval, $T_{INT}$, following the delivery of stimulation signal 210A. IMD 16 delivers stimulation signal 210B at the expiration of the inter-therapy interval $T_{INT}$. By not delivering stimulation during $T_{INT}$, muscle fatigue may be minimized in comparison to delivering stimulation substantially continuously during a therapy interval. An inter-therapy interval, such as $T_{INT}$, may be approximately 10 seconds in some examples. In other examples, an inter-therapy interval may be more or less than 10 seconds. In any case, the purpose of an inter-therapy interval is to deliver no or minimal stimulation so as to minimize muscle fatigue.

FIGS. 13A-13C illustrate example stimulation signals that IMD 16 may deliver as part of the second stimulation therapy in an adaptive fashion so as to minimize muscle fatigue. In particular, FIGS. 13A-13C illustrate example stimulation signals 220, 230, and 240, respectively. Stimulation signals 220, 230, and 240 may be delivered sequentially. In particular, stimulation signals 230 and 240 may be delivered within an inter-therapy interval (e.g., about 30 seconds) of the previous stimulation signal that was delivered as part of the second stimulation therapy. That is stimulation signal 230 may be delivered after expiration of the inter-therapy interval that began after delivery of stimulation signal 220 and stimulation signal 240 may be delivered after expiration of the inter-therapy interval that began after delivery of stimulation signal 230.

As discussed with respect to FIG. 10, in some examples, processor 50 adjusts one or more parameters of the second stimulation therapy if IMD 16 has previously delivered the second stimulation therapy within the interval of time. Adjusting one or more parameters of the second stimulation therapy help minimize patient adaptation to the second stimulation therapy, as well as any muscle fatigue that may result from the second stimulation therapy. FIGS. 13A-1C provide an example of adaptive second stimulation therapy in which, for each subsequent stimulation signal triggered within an inter-therapy interval of the previous second stimulation therapy delivery period, the duration of fast-twitch muscle stimulation decreases by a predetermined amount, e.g., five seconds.

In FIGS. 13A-13C the stimulation pulses that stimulate fast-twitch muscles are the stimulation pulses of relatively high frequency, i.e., bursts 222, 232, and 242. As shown in FIGS. 13B and 13C, the time interval 233 for stimulation pulses 232 has decreased in comparison to the time interval 223 for stimulation pulses 222, and the time interval 243 for stimulation pulses 242 has decreased in comparison to timer interval 233 for stimulation pulses 232. Accordingly, the time interval 235 for relatively low frequency stimulation pulses 234 has increased in comparison to the time interval 225 for relatively low frequency stimulation pulses 224, and the time interval 245 for relatively low frequency stimulation pulses 244 has increased in comparison to timer interval 235 for stimulation pulses 234.

Because the time interval for the high frequency stimulation pulses decreases and the time interval for the low frequency stimulation pulses increases for each subsequent stimulation signal, the duration of time that the fast twitch muscles are activated is minimized, which may help minimize muscle fatigue.

FIGS. 14A-14C illustrate another set of example of stimulation signals IMD 16 may generate and deliver as part of adaptive stimulation therapy to help minimize muscle fatigue. In particular, FIGS. 14A-14C illustrate example stimulation signals 250, 260, and 270, respectively. As with the example stimulation signals shown in FIGS. 13A-13C, stimulation signals 250, 260, and 270 may be delivered sequentially, e.g., such that signal 260 is delivered subsequent to signal 250, and signal 270 is delivered subsequent to signal 260.

Signals 250, 260, and 270 in FIGS. 14A-14C are also similar to the signals in FIGS. 13A-C in the sense that, for each subsequent signal, the number of high frequency stimulation pulses decreases and the number of low frequency stimulation pulses increases. However, the manner in which processor 50 of IMD 16 adjusts the signals 250, 260, and 270 over time is different than that for signals 220, 230, and 240. Specifically, for each subsequently delivered signal, a first portion of the relatively high frequency stimulation pulses is replaced with relatively low frequency stimulation pulses compared to the previous signal.

In FIGS. 14A-14C, $T_1$ defines an interval during which bursts of relatively high frequency stimulation pulses are delivered during delivery of standard second stimulation therapy, i.e., non-adaptive second stimulation therapy. Interval $T_2$ defines an interval during which relatively low frequency stimulation pluses are delivered for both non-adaptive and adaptive second stimulation therapy. When processor 50 modifies the stimulation signals to provide adaptive second stimulation therapy, processor 50 replaces, for each subsequent signal, a first portion of the high frequency stimulation pulses with low frequency stimulation pulses. The time interval within $T_1$ during which processor 50 delivers low frequency stimulation pulses is labeled $T_3$.

Accordingly, stimulation signal 250 in FIG. 14A includes relatively high frequency stimulation pulses 252 during interval $T_1$, and relatively low frequency stimulation pulses during interval $T_2$. Example stimulation signal 260 in FIG. 14B represents an adapted stimulation signal delivered subsequent to signal 250. Signal 260 includes relatively low frequency stimulation pulses 266 that precede the relatively high frequency stimulation pulses 262 during interval $T_1$. Relatively low frequency stimulation pulses 266 are delivered over interval $T_3$ within interval $T_1$. If processor 50 determines that another therapy period of the second stimulation therapy is desirable after signal 260 is delivered to patient 14, processor 50 may further adapt stimulation signal 260.

In the example shown in FIG. 14C, processor 50 modifies stimulation signal 260 such that relatively low frequency stimulation pulses 276, which precede relatively high frequency stimulation pulses 272 during interval $T_1$, are delivered for approximately twice as long as the relatively low frequency stimulation pulses 266 that precede the relatively high frequency stimulation pulses 262 in stimulation signal 260. That is, the duration of interval $T_3$ for stimulation signal 270 is approximately twice the duration of interval $T_3$ for stimulation signal 260. Interval $T_3$ may generally be selected to have an initial value and to increase for each subsequent adaptive stimulation signal by that initial value. In this way, $T_3$ increases in a way that may allow effective therapy to be delivered while minimizing muscle fatigue. The initial value of interval $T_3$ may be a fraction of interval $T_1$ and, more particularly, may be selected to allow a number of adaptive stimulation signal to be delivered before the value of $T_3$ approaches the value of $T_1$. Other values for $T_3$ and algorithms for modifying the value of $T_3$ for delivering adaptive stimulation are contemplated.

Although not shown in FIGS. 14A-14C, in some examples, this adaptive pattern may continue for subsequently delivered stimulation pulses until low frequency stimulation pulses have replaced all relatively high frequency stimulation pulses during interval $T_1$, or, in other words, until the interval $T_3$ equals interval $T_1$. In such examples, any subsequently delivered stimulation pulses may include only low frequency stimulation pulses. In other examples, however, processor 50 may continue to adjust the stimulation signal, but maintain at least some relatively high frequency stimulation signals to activate the fast twitch muscle fibers. Processor 50 may reset the adaptive pattern of stimulation signals after a certain period of time of not triggering the second stimulation therapy. That is, processor 50 may deliver the second stimulation in an adaptive fashion when the second stimulation is triggered within a therapy interval, and continue to deliver second stimulation in an adaptive fashion as long as the second stimulation is triggered within consecutive therapy intervals. However, when second stimulation therapy is not triggered during a therapy interval, processor 50 may reset the adaptive pattern so that the next time second stimulation therapy is delivered in accordance with a non-adapted signal, e.g., signal 250.

The example stimulation signals shown in FIGS. 13A-13C and 14A-14C are merely examples. The purpose of these signals is to provide working examples to demonstrate the described techniques for providing two different types of stimulation therapy to manage patient incontinence.

In some cases, patient 14 may perceive the delivery of the second stimulation therapy or the transition from the delivery of the first stimulation therapy to the delivery of the second stimulation therapy, e.g., when the first and second stimulation therapies are delivered at different times (e.g., in a non-overlapping manner). Because the stimulation signals associated with the second stimulation therapy may have a higher intensity (e.g., a higher amplitude or frequency) than the stimulation signals associated with the first stimulation therapy, the initiation of the second stimulation therapy may cause discomfort to patient 14. The discomfort may or may not exceed a pain threshold of patient 14.

In order to help minimize the discomfort to patient 14 from the delivery of the second stimulation therapy or the transition from the first stimulation therapy to the second stimulation therapy, processor 50 of IMD 16 (FIG. 3) or a processor of another device (e.g., programmer 24) may control therapy module 52 (FIG. 3) of IMD 16 to gradually modify one or more stimulation parameter values (e.g., amplitude or frequency) over time, rather than abruptly (e.g., instantaneously) increase the parameter values relative to the one or more stimulation parameter values defined by the first stimulation therapy. That is, upon determining that delivery of the second stimulation therapy is desirable, e.g., in response to a sensed physiological condition or patient input, processor 50 of IMD 16 (or another device) may control therapy delivery module 52 to deliver therapy to patient 14 by gradually transitioning between the one or more stimulation parameter values of the first stimulation therapy to the one or more stimulation parameter values of the second stimulation therapy. In some examples, the transition from the first stimulation therapy delivery to the second stimulation therapy includes a ramping up of the amplitude and frequency of the stimulation signals. The amplitude, frequency or other stimulation parameter value (e.g., pulse width in the case of stimulation pulses) may be modified in a linear, nonlinear, exponential or step-wise manner.

Similarly, upon determining termination of the second stimulation therapy delivery is desirable (e.g., because of the termination of the therapy period or because of patient input indicating abortion of the second stimulation therapy is desirable), processor 50 (or another processor) may control therapy delivery module 52 to gradually transition from therapy delivery according to the one or more stimulation parameter values of the second stimulation therapy to the one or more stimulation parameter values of the first stimulation therapy. In some examples, the transition from the second stimulation therapy delivery to the first stimulation therapy includes a ramping down of the amplitude and frequency of the stimulation signals.

The gradual ramping upward or downward of the one or more stimulation parameter values is contrary to an instantaneous modification to the one or more stimulation parameter values. An immediate change in a stimulation parameter value may be characterized by, for example, a jump from therapy delivery according to a first stimulation parameter value to therapy delivery according to a second stimulation parameter value. In contrast, a gradual change in the stimulation parameter value may be accomplished by, for example, shifting from a stimulation parameter value defined by the first stimulation therapy to therapy delivery according to a second stimulation parameter value defined by the second stimulation therapy over time. The shift from the first stimulation parameter value to the second stimulation parameter value may involve, for example, therapy delivery according to intermediate stimulation parameter values between the first and second stimulation parameter values.

Various techniques may be used to transition between stimulation parameter values of the first and second stimulation therapies. In some examples, processor 50 of IMD 16 (or another device) utilizes a predetermined constant or variable rate of change to gradually ramp up or down between the stimulation parameter values (e.g., the amplitude and/or frequency) of the first and second stimulation therapies. In other examples, processor 50 may gradually increase or decrease a stimulation parameter value over a predetermined range of time (referred to as a transition time). By gradually adjusting a stimulation parameter value to a desired level over time rather than making an adjustment to a desired value substantially immediately, IMD 16 may effectively adjust the stimulation parameter value without patient 14 experiencing undesirable side effects that may result from making abrupt changes to a stimulation parameter, such as stimulation amplitude, too quickly.

In some cases, the first and second stimulation therapies define different stimulation signal amplitudes. Processor 50 of IMD 16 (or a processor of another device, such as programmer 24) may control therapy module 52 to shift from the first stimulation therapy to the second stimulation therapy by gradually shifting from a baseline amplitude (defined by the first stimulation therapy) to a second amplitude (defined by the second stimulation therapy) according to a predetermined pattern. Example patterns include, but are not limited to, a linear, non-linear or exponential rate of change. That is, processor 50 (or another processor) may gradually ramp the amplitude up or down using a linear, non-linear or exponential rate of change.

Similarly, in some cases, the first and second stimulation therapies define different stimulation signal frequencies in addition to or instead of the different amplitudes. Processor 50 of IMD 16 (or a processor of another device, such as programmer 24) may control therapy module 52 to shift from the first stimulation therapy to the second stimulation therapy by gradually shifting from a baseline frequency (defined by the first stimulation therapy) to a second frequency (defined by the second stimulation therapy) according to a predetermined pattern. Example patterns include, but are not limited to, a linear pattern, a nonlinear pattern or an exponential pattern. In addition, in some examples, patterns such as a step-wise pattern may be used to transition between stimulation parameter values.

In examples in which the first and second stimulation therapies define different stimulation signal frequencies and different amplitudes, processor 50 of IMD 16 (or another processor) may modify one or both the frequency and/or amplitude values at a time. For example, if the second stimulation therapy defines greater amplitude and frequency values than the first stimulation therapy, processor 50 may control therapy module 52 to gradually increase the stimulation amplitude over time (e.g., using a predetermined rate of change, as defined by a predetermined pattern, or over a predetermined duration of time) while maintaining the frequency defined by the first stimulation therapy. After the stimulation amplitude has reached a second amplitude value defined by the second stimulation therapy, processor 50 may deliver stimulation therapy according to the second amplitude value while controlling therapy module 52 to gradually increase the frequency over time until the frequency value of the second stimulation therapy is achieved.

In other examples, processor 50 may control therapy module 52 to gradually increase the stimulation signal frequency over time while maintaining a first amplitude value defined by the first stimulation therapy. After the frequency has reached a second frequency value defined by the second stimulation therapy, processor 50 may deliver stimulation therapy to patient 14 according to the second frequency while controlling therapy module 52 to gradually increase the amplitude over time until the amplitude value of the second stimulation therapy is achieved.

In other examples in which the first and second stimulation therapies define different stimulation parameter values, processor 50 of IMD 16 (or another processor) may modify all of the stimulation parameter values at the same time. In some cases, one of the stimulation parameter values is gradually changed over time while another is instantaneously changed. For example, upon determining the delivery of the second stimulation therapy is desirable, processor 50 of IMD 16 (or another processor) may gradually increase the stimulation amplitude (e.g., using a predetermined rate of change or over a predetermined duration of time) while applying the frequency of the second stimulation therapy at the onset of the second stimulation therapy delivery. That is, processor 50 controls therapy module 52 to shift to the frequency of the second stimulation therapy immediately upon determining delivery of the second stimulation therapy is desirable.

In other examples, upon determining the delivery of the second stimulation therapy is desirable, processor 50 of IMD 16 (or another processor) may gradually increase the stimulation frequency (e.g., using a predetermined rate of change, as defined by a predetermined pattern, or over a predetermined duration of time) while applying the amplitude of the second stimulation therapy at the onset of the second stimulation therapy delivery. In this way, processor 50 controls therapy module 52 to shift to the amplitude value of the second stimulation therapy immediately upon determining delivery of the second stimulation therapy is desirable.

While techniques for transitioning from the first stimulation therapy to the second stimulation therapy are described above, similar techniques may also be applied to transitioning from the second stimulation therapy to the first stimulation therapy upon determining the termination of the second stimulation therapy is desirable. As previously indicated, the first stimulation therapy periodically over an extended period of time, e.g., chronic stimulation and the second stimulation therapy is periodically delivered to patient 14 to provide a short-term boost to the effectiveness of the first stimulation therapy. Thus, termination of the second stimulation therapy may be desirable after a predetermined therapy period in which the second stimulation therapy is delivered (in an overlapping or non-overlapping manner with the first stimulation therapy) or in response to patient input indicating the termination of the second stimulation therapy is desirable.

Other techniques may be used to minimize patient comfort resulting from the onset of the second stimulation therapy instead or in addition to gradually ramping up or down of one or stimulation parameter values when transitioning between the first and second stimulation therapies. In some examples, IMD 16 may implement prepulse inhibition in order to minimize the perception of the shift between the stimulation parameter values of the first stimulation therapy to the increased stimulation parameter values of the second stimulation therapy. Prepulse inhibition is a neurological phenomenon in which a weaker prestimulus (also referred to as a prepulse) inhibits the reaction of an organism to a subsequent stronger stimulus (e.g., a stimulation signal of the second stimulation therapy).

Figure 15:
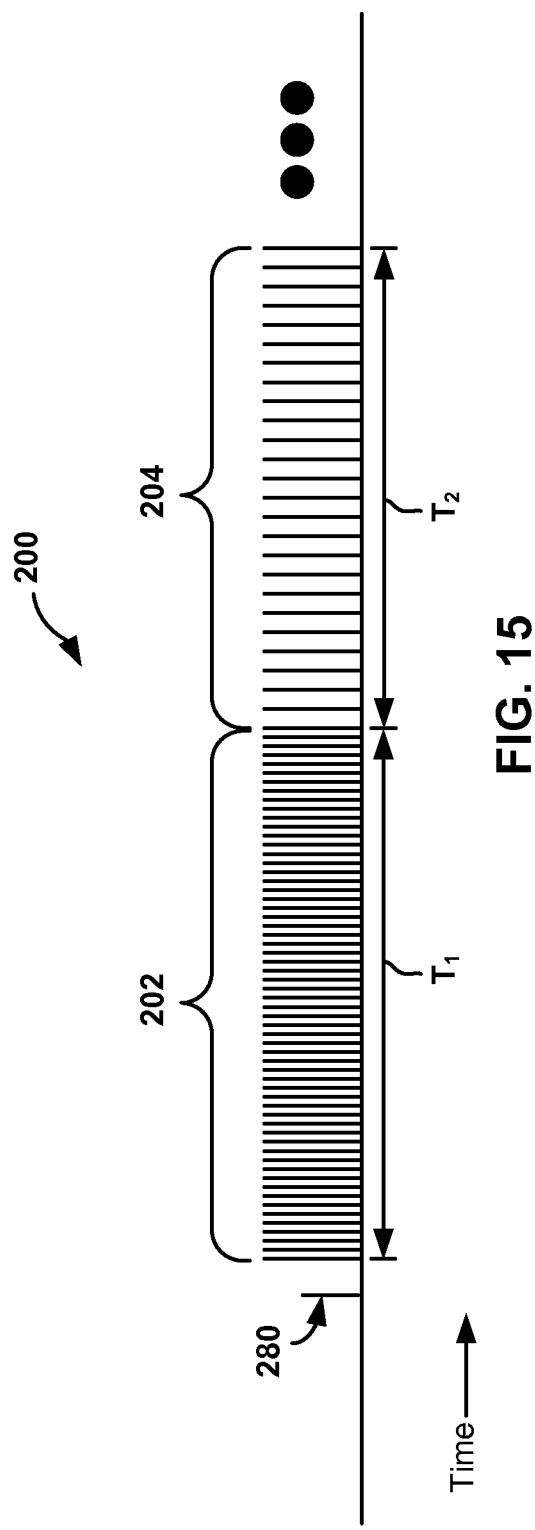
FIG. 15 illustrates an example prestimulus that is delivered prior to the second stimulation therapy.

FIG. 15 is a conceptual illustration of example stimulation signals that therapy delivery module 52 of IMD 16 may generate and deliver as part of the second stimulation therapy. In the example shown in FIG. 15, the IMD 16 delivers prestimulus 280 prior to delivering stimulation signal 200, which generates the second physiological effect (e.g., promotion of internal urinary sphincter contraction) associated with the second stimulation therapy. As described with respect to FIG. 11, in some examples, stimulation signal 200 includes stimulation pulses 202 and stimulation pulses 204, which have a lower frequency than stimulation pulses. Other stimulation signals may be used instead of or in addition to stimulation signal 200 to provide the second stimulation therapy.

Prestimulus 280 includes one or more stimulation signals (e.g., pulses) that are delivered before each therapy period of the second stimulation therapy in order to substantiate the central perception inhibition effect. In the example shown in FIG. 15, prestimulus 280 includes a single stimulation pulse that is delivered about 1 ms to about 25 ms prior to the delivery of stimulation signal 200. If the second stimulation therapy is delivered for more than one consecutive therapy period, e.g., as described with respect to FIG. 12, processor 50 of IMD 16 (or another device) may control therapy module 52 to deliver prestimulus 280 prior to each therapy period.

In general, prestimulus 280 includes one or more stimulation signals having a smaller intensity than stimulation signal 200 delivered as part of the second stimulation therapy. Stimulation intensity may be a function of, e.g., defined by, for example, the amplitude and/or frequency of a stimulation signal. In the example shown in FIG. 15, prestimulus 280 includes a single stimulation pulse that has an amplitude that is about 0.10 to 0.50 of the amplitude of the stimulation signals 200. In other examples, IMD 16 can deliver a single prepulse (e.g., as shown in FIG. 15) or a prestimulus train of pulses similar to pulse 280 shown in FIG. 15 (e.g., about two to about 100 pulses) to patient 14 before the first stimulation therapy period of a plurality of consecutive second stimulation therapy periods, or during a second stimulation therapy period, rather than before each therapy period as described with respect to FIG. 15.

In addition to or instead of the gradual modification of stimulation parameter values and the prepulse inhibition, electrical nerve block may be used to minimize discomfort to patient 14 that may result from the delivery of the second stimulation therapy. For example, IMD 16 may deliver a relatively high frequency stimulation via one or more electrodes 29 (FIG. 3) or a separate set of electrodes to a tissue site proximal to the target stimulation site for the second stimulation therapy (e.g., a tissue site closer to the spinal cord than the target stimulation site) and along the same nerve targeted by the second stimulation therapy. Electrical nerve block may help block conduction along the nerve to minimize perception of the delivery of the second stimulation therapy by patient 14.

The nerve block may be achieved via a high frequency stimulation signal having a frequency of about 200 Hz to about 20 kHz, although other frequency ranges are contemplated and may be specific to patient 14. Delivery of high frequency nerve block may be useful to initiate a relatively rapid onset of nerve conduction that is temporally correlated with the delivery of the second stimulation therapy, thereby providing relevant nerve conduction block. In some examples, processor 50 of IMD 16 (or another device) may control therapy module 52 to initiate the delivery of the high frequency stimulation to achieve the nerve block before or at the onset of the second stimulation therapy. In some examples, the high frequency nerve block may be maintained throughout the delivery of the second stimulation therapy period. In other examples, a device separate from IMD 16 may deliver the stimulation to block nerve conduction. In addition, nerve block stimulation other than high frequency stimulation, such as anodal block stimulation, may also be used.

Other techniques may also be used to minimize discomfort to patient 14 that may result from the delivery of the second stimulation therapy in addition to or instead of the techniques described above. In some examples, other innocuous stimulation is delivered before or at the onset of the second stimulation therapy. For example, in some examples, an outer housing of IMD 16 vibrates during the second stimulation therapy period in order to help minimize the discomfort to patient 14. The vibration of outer housing of IMD 16 may produce paresthesia near the target tissue site for the second stimulation therapy in examples in which IMD 16 is implanted near the target tissue site. IMD 16 may vibrate at a frequency of about 1 Hz to about 200 Hz, although other frequency ranges are contemplated.

In yet other examples, IMD 16 or another device delivers stimulation to tissue sites within patient 14 other than the target tissue site for the second stimulation therapy in order to minimize the discomfort to patient 14 from the delivery of the second stimulation therapy. Different stimulation frequencies for the delivery of stimulation to the relevant tissue site (which may be internal or external) may elicit different patient responses. For example, a relatively low frequency stimulation may activate muscle tissue and/or reduce pain resulting from the second stimulation therapy by stimulating the production of endogenous endorphins, and a relatively high frequency stimulation may produce paresthesia.

In some examples, IMD 16 or another device (e.g., a separate microstimulator or external medical device coupled to external or subcutaneous electrodes) delivers stimulation to a dermatome associated with the target nerve for the second stimulation therapy (e.g., a hypogastric nerve, a pudendal nerve, a dorsal penile nerve in a male patient, a dorsal clitoral nerve in a female patient). A dermatome can be an area of skin that is supplied by the target nerve. Delivery of stimulation to the dermatome may, for example, produce paresthesia or produce endogenous endorphins that help reduce pain perceived by patient 14. In examples in which IMD 16 delivers the stimulation to the dermatome, IMD 16 can deliver the stimulation to the dermatome using select electrodes of a lead that is separate from the lead (e.g., lead 28 in FIG. 1) that delivers the second stimulation therapy to patient 14.

As another example, for female patients, a vaginal plug can be used to deliver stimulation during the second stimulation therapy period in order to help minimize the discomfort to patient 14, e.g., by producing paresthesia. If a device separate from IMD 16 is used to deliver the stimulation to patient 14 that is used to minimize discomfort to patient 14, the separate device may be external or implanted within patient 14, and may communicate with IMD 16 via a wired connection or a wireless communication technique (e.g., RF communication techniques).

The techniques described in this disclosure may reduce or substantially eliminate leaking episodes caused by urinary incontinence. That is, by delivering first stimulation therapy to modulate nerve afferent activities to inhibit bladder contraction, or to maintain internal urinary sphincter closure or urethral closure and, when triggered, second stimulation therapy configured to maximize closure of the internal urinary sphincter, external urinary sphincter, and/or the periurethral muscles, improved management of urinary incontinence may be achieved. The techniques described above may also provide advantageous features that allow a patient to control the delivery of the second stimulation therapy. For example, the patient may actively trigger delivery of the second stimulation therapy or may manually abort the second stimulation therapy. The patient may also temporarily inhibit or deactivate the second stimulation therapy when voiding voluntarily.

The techniques described in this disclosure may reduce or substantially eliminate leaking episodes caused by fecal incontinence. In fecal incontinence examples, the IMD may deliver first stimulation therapy to, for example, a sacral nerve to improve internal and/or external anal sphincter muscle tone, and deliver second stimulation therapy to, for example, a sacral nerve, an internal sphincter, or an external sphincter. The first stimulation therapy may help to close or maintain internal sphincter closure or improve internal and/or external anal sphincter muscle tone. The second stimulation therapy may promote contraction of the internal anal sphincter and/or the external anal sphincter.

Similar to the therapy techniques described with respect to urinary incontinence, the first stimulation therapy may be delivered on a regular basis, e.g., to improve muscle tone, and the second stimulation therapy may be viewed as a short term boost to the effectiveness of the first stimulation therapy or to close or promote closure of the internal and/or external anal sphincter. The second stimulation therapy may be delivered in response to detecting a trigger event, such as receiving patient input, detecting a patient parameter indicative of an imminent fecal incontinence event, or detecting a patient parameter indicative of an increased probability of a fecal incontinence event. Example patient parameters may include contraction of the anal sphincter, patient activity level, or patient posture state. The IMD may detect contraction of the anal sphincter using a pressure sensor, an EMG sensor, or any other suitable sensing mechanism.

In some examples, the disclosure is directed to a method comprising delivering, with a medical device, first electrical stimulation therapy to a patient to generate a first physiological effect, receiving input from the patient or a sensor while the medical device is delivering the first electrical stimulation therapy, and delivering, with the medical device, second electrical stimulation therapy to the patient based on the input from the patient or the sensor, wherein the delivery of the second electrical stimulation therapy generates a second physiological effect that is different than the first physiological effect, and wherein the first and second electrical stimulation therapies are configured to manage one of urinary incontinence or fecal incontinence.

In some examples of the method, the first physiological effect comprises inhibiting contraction of a bladder of the patient, and the second physiological effect comprises promoting contraction of one or more of a bladder outlet of the patient, an internal urinary sphincter of the patient, an external urinary sphincter of the patient, or periurethral muscles of the patient. In addition, in some examples of the method, the first electrical stimulation therapy is delivered to the patient on a regular basis and the second electrical stimulation therapy is delivered to the patient only when the input from the patient or the sensor is indicative of at least one of an imminent involuntary voiding event or an increased possibility of an occurrence of an involuntary voiding event.

In some examples of the method, delivering the second electrical stimulation therapy comprises delivering a plurality of electrical stimulation signals during a plurality of therapy periods that are separated by a minimum inter-therapy interval to minimize muscle fatigue.

In some examples of the method, delivering the first electrical stimulation therapy comprises delivering the first electrical stimulation therapy to at least one of a pudendal nerve or a sacral nerve, and delivering second electrical stimulation comprises delivering second electrical stimulation to at least one of a hypogastric nerve, the pudendal nerve, the sacral nerve, a dorsal penile nerve, a dorsal clitoral nerve, an external urinary sphincter, or periurethral muscles.

In some examples of the method, delivering the second electrical stimulation therapy comprises delivering the second electrical stimulation therapy for a therapy period of approximately 10 seconds to approximately 50 seconds.

In some examples of the method, the delivering the second electrical stimulation therapy comprises delivering a stimulation signal comprising an amplitude of approximately two to approximately four times rheobase of a target muscle or nerve, a frequency of approximately 15 Hertz to approximately 66 Hertz, and a pulse width of approximately 100 microseconds to approximately 1000 microseconds.

In some examples of the method, delivering the second electrical stimulation therapy comprises delivering the second electrical stimulation therapy according to a first set of stimulation parameters for a period of time and delivering the second electrical stimulation therapy according to a second set of stimulation parameters different that the first set of stimulation parameters for a subsequent period of time. In some examples of the method, the first set of stimulation parameters is configured to activate fast-twitch muscles of the patient, and the second set of stimulation parameters is configured to activate slow-twitch muscles of the patient.

In some examples of the method, delivering second electrical stimulation therapy to the patient based on the input from the patient or the sensor comprises delivering second electrical stimulation therapy for a predetermined period of time based on the patient input.

In some examples of the method, delivering second electrical stimulation therapy to the patient based on the input from the patient or the sensor comprises determining whether the input is indicative of a trigger event for the second stimulation therapy, determining whether a number of trigger events detected within a predetermined interval of time is greater than or equal to a threshold value, and delivering the second electrical stimulation therapy to the patient if the number of trigger events detected within the predetermined interval of time is not greater than or equal to the threshold value. In some examples, the method further comprises generating a patient notification if the number of trigger events detected within the predetermined interval of time is greater than or equal to the threshold value.

In some examples of the method, the input from the sensor is indicative of at least one of bladder contraction or detrusor muscle activity. In some examples, the input from the sensor comprises at least one of a bladder impedance value, a current or voltage amplitude value for a sacral or pudendal afferent nerve signal, or an electromyogram for a muscle in a pelvic region of the patient.

In some examples of the method, the input from the sensor is indicative of patient activity level or patient posture. In addition, in some examples of the method, the input includes sensor input, and the method further comprises determining whether the input is indicative of a trigger event for the second stimulation therapy, generating a patient notification that indicates prospective delivery of the second stimulation therapy if the input is indicative of the trigger event, receiving patient input after generating the patient notification, and suspending the delivery of the second electrical stimulation therapy based on the patient input.

In some examples of the method, delivering the second electrical stimulation therapy to the patient based on the input from the patient or the sensor comprises determining whether a first input is indicative of a trigger event for the second stimulation therapy, delivering the second electrical stimulation therapy to the patient for a first therapy period if the first input is indicative of the trigger event, after the first therapy period, receiving a second input from the patient or the sensor, after the first therapy period, determining whether the second input is indicative of the trigger event, delivering the second electrical stimulation therapy to the patient for a second therapy period if the second input is indicative of the trigger event, and deactivating the second electrical stimulation therapy if the second input is not indicative of the trigger event.

In some examples of the method, delivering the second electrical stimulation therapy to the patient based on the input from the patient or the sensor comprises determining whether the second stimulation therapy was delivered to the patient within an immediately preceding period of time, delivering the second electrical stimulation therapy to the patient if the second stimulation therapy was not delivered to the patient within the immediately preceding period of time, adjusting the second electrical stimulation therapy if the stimulation therapy was delivered to the patient within the immediately preceding period of time, and delivering the adjusted second electrical stimulation therapy to the patient. In some examples, delivering the second electrical stimulation therapy comprises delivering first stimulation pulses for a first period of time and delivering second stimulation signals having a lower frequency than the first stimulation signals for a second period of time, wherein adjusting the second stimulation therapy comprises adjusting the duration of one of the first period of time or the second period of time.

In some examples of the method, delivering the second electrical stimulation therapy to the patient comprises gradually increasing or decreasing a first stimulation parameter value defined by the first electrical stimulation therapy to a second stimulation parameter value defined by the second electrical stimulation therapy according to a predetermined rate of change or over a predetermined duration of time.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises instantaneously shifting stimulation delivery from the second value to the fourth value of the second stimulation parameter upon receiving the input and gradually shifting from the first value to the third value of the first stimulation parameter value according to a predetermined rate of change or over a predetermined duration of time.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises gradually shifting from the first value to the third value of the first stimulation parameter value according to a first predetermined rate of change or over a first predetermined duration of time and gradually shifting from the second value to the fourth value of the second stimulation parameter value according to a second predetermined rate of change or over a second predetermined duration of time, wherein the first and second predetermined rates of change are different and the first and second predetermined durations of time are different.

In some examples of the method, the first electrical stimulation therapy defines a first value of a first stimulation parameter and a second value of a second stimulation parameter and the second electrical stimulation therapy defines a third value of the first stimulation parameter and a fourth value of the second stimulation parameter, and delivering the second electrical stimulation therapy to the patient comprises gradually transitioning therapy delivery from the first value to the third value of the first stimulation parameter value and subsequently gradually transitioning therapy delivery from the second value to the fourth value of the second stimulation parameter value.

In some examples of the method, the method further comprises delivering a prestimulus before delivering the second stimulation therapy. In some examples, the prestimulus comprises at least one stimulation pulse comprising an amplitude of about 0.10 to about 0.50 of an amplitude of a stimulation signal defined by the second electrical stimulation therapy. In addition, in some examples, delivering the prestimulus comprises delivering the prestimulus about 1 millisecond to about 25 milliseconds before delivering the second electrical stimulation therapy.

In some examples of the method, the method further comprises delivering stimulation to block nerve conduction while delivering the second electrical stimulation therapy. In some examples, delivering the stimulation to block nerve conduction comprises delivering a stimulation signal having a frequency of about 200 Hertz to about 20 kilohertz. In addition, in some examples, delivering second electrical stimulation therapy to the patient comprises delivering the second electrical stimulation therapy to a target nerve, and wherein delivering stimulation to block nerve conduction comprises delivering stimulation to block conduction of the target nerve.

In some examples of the method, the method further comprises delivering a third electrical stimulation therapy to minimize discomfort to the patient while delivering the second electrical stimulation therapy. In some examples, delivering second electrical stimulation therapy to the patient comprises delivering the second electrical stimulation therapy to a target nerve and delivering the third electrical stimulation therapy comprises delivering the third electrical stimulation therapy to a dermatome associated with the target nerve.

In other examples, the disclosure is directed to a computer-readable comprising instructions that cause a programmable processor to control a therapy delivery module to deliver a first electrical stimulation therapy to a patient to generate a first physiological effect, receive input from the patient or a sensor while the therapy delivery module is delivering the first electrical stimulation therapy, and control the therapy delivery module to deliver a second electrical stimulation therapy to the patient based on the input from the patient or the sensor, wherein the delivery of the second electrical stimulation therapy generates a second physiological effect that is different than the first physiological effect, and wherein the first and second electrical stimulation therapies are configured to manage one of urinary incontinence or fecal incontinence.

The techniques described in this disclosure, including those attributed to programmer 24, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 24, any one or more parts of the techniques described herein may be implemented by a processor of one of IMD 16, programmer 24, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

What is claimed is:

1. A medical system comprising:
   a therapy delivery module configured to generate and deliver a first electrical stimulation therapy to a patient to generate a first physiological effect and a second electrical stimulation therapy to the patient to generate a second physiological effect that is different than the first physiological effect; and
   a processor configured to:
      control the therapy delivery module to deliver the first electrical stimulation therapy chronically to the patient over a period of time; and
      control, during the period of time, the therapy delivery module to deliver the second electrical stimulation therapy temporarily only in response to received input, wherein the first and second electrical stimulation therapies are configured to reduce a likelihood of at least one of urinary voiding events or fecal voiding events.

2. The medical system of claim 1, wherein the therapy delivery module is configured to generate the first electrical stimulation therapy according to a first set of stimulation parameters and generate the second electrical stimulation therapy according to a second set of stimulation parameter set, the first set of stimulation parameters being different than the second set of stimulation parameters.

3. The medical system of claim 2, wherein the first set of stimulation parameters comprise a first set of electrodes and the second set of stimulation parameters comprise a second set of electrodes different than the first set of electrodes.

4. The medical system of claim 1, wherein the processor is configured to control, in response to the received input, the therapy delivery module to deliver the second electrical stimulation therapy instead of the first electrical stimulation therapy.

5. The medical system of claim 4, wherein the processor is configured to control the therapy delivery module to deliver the second electrical stimulation therapy to the patient for a predetermined period of time following the received input.

6. The medical system of claim 5, wherein the processor is configured to control, in response to completion of the predetermined period of time, the therapy delivery module to deliver the first electrical stimulation therapy to the patient instead of the second electrical stimulation therapy.

7. The medical system of claim 1, wherein the processor is configured to control, in response to the received input, the therapy delivery module to deliver the second electrical stimulation therapy overlapping in time with delivery of the first electrical stimulation therapy.

8. The medical system of claim 1, wherein the processor is configured to control the therapy delivery module to deliver the first electrical stimulation therapy as an open loop therapy.

9. The medical system of claim 1, wherein the processor is configured to control the therapy delivery module to deliver the first electrical stimulation therapy on a regular basis over the period of time.

10. The medical system of claim 1, further comprising a sensor configured to at least one of sense a patient parameter indicative of a bladder condition or a detrusor muscle activity, or generate a signal indicative of patient activity or posture, wherein the processor is configured to receive the input from the sensor.

11. The medical system of claim 1, further comprising a user input mechanism configured to receive input from a user indicative of at least one of an imminent involuntary voiding event of the patient or an increased possibility of an occurrence of an involuntary voiding event of the patient, wherein the processor is configured to receive the input from the user input mechanism.

12. The medical system of claim 1, wherein the therapy delivery module is configured to deliver the second electrical stimulation according to a first set of stimulation parameters for a first portion of time and according to a second set of stimulation parameters different than the first set of stimulation parameters for a second portion of time subsequent to the first portion of time.

13. A method comprising:
controlling, by a processor, a therapy delivery module to deliver first electrical stimulation therapy chronically to a patient over a period of time to generate a first physiological effect;
receiving input via the patient or a sensor; and
controlling, by the processor and during the period of time, the therapy delivery module to deliver second electrical stimulation therapy temporarily to the patient only in response to the input received from the patient or the sensor, wherein the delivery of the second electrical stimulation therapy generates a second physiological effect that is different than the first physiological effect, and wherein the first and second electrical stimulation therapies are configured to reduce a likelihood of at least one of urinary voiding events or fecal voiding events.

14. The method of claim 13, wherein:
controlling the therapy delivery module to deliver the first electrical stimulation therapy comprises controlling the therapy delivery module to deliver the first electrical stimulation therapy according to a first set of stimulation parameters; and
controlling the therapy delivery module to deliver the second electrical stimulation therapy comprises controlling the therapy delivery module to deliver the second electrical stimulation therapy according to a second set of stimulation parameters, the first set of stimulation parameters being different than the second set of stimulation parameters.

15. The method of claim 14, wherein the first set of stimulation parameters comprise a first set of electrodes and the second set of stimulation parameters comprise a second set of electrodes different than the first set of electrodes.

16. The method of claim 13, wherein controlling the therapy delivery module to deliver the second electrical stimulation therapy comprises controlling, in response to the received input, the therapy delivery module to deliver the second electrical stimulation therapy instead of the first electrical stimulation therapy.

17. The method of claim 13, wherein controlling the therapy delivery module to deliver the second electrical stimulation therapy comprises controlling, in response to the received input, the therapy delivery module to deliver the second electrical stimulation therapy overlapping in time with delivery of the first electrical stimulation therapy.

18. The method of claim 13, wherein controlling the therapy delivery module to deliver the first electrical stimulation therapy comprises controlling the therapy delivery module to deliver the first electrical stimulation therapy as an open loop therapy.

19. The method of claim 13, wherein controlling the therapy delivery module to deliver the first electrical stimulation therapy chronically to the patient comprises controlling the therapy delivery module to deliver the first electrical stimulation therapy to the patient on a regular basis over the period of time.

20. The method of claim 13, further comprising sensing, via one or more sensors, a patient parameter indicative of a bladder condition or a detrusor muscle activity, or generate a signal indicative of patient activity or posture, and wherein the method further comprises receiving, by the processor, the input from the sensor.

21. The method of claim 13, further comprising receiving, by the processor, the input from a user input mechanism configured to receive input from a user indicative of at least one of an imminent involuntary voiding event of the patient or an increased possibility of an occurrence of an involuntary voiding event of the patient.

22. The method of claim 13, wherein an implantable medical device comprises the therapy delivery module and the processor.

23. A system comprising:
means for generating and delivering electrical stimulation therapy to a patient, the electrical stimulation therapy comprising a first electrical stimulation therapy to generate a first physiological effect and a second electrical stimulation therapy to the patient to generate a second physiological effect that is different than the first physiological effect;
means for controlling the means for generating and delivering electrical stimulation therapy to deliver the first electrical stimulation therapy chronically to the patient over a period of time; and
means for controlling, during the period of time, the means for generating and delivering electrical stimulation therapy to deliver the second electrical stimulation therapy temporarily only in response to received input, wherein the first and second electrical stimulation therapies are configured to reduce a likelihood of at least one of urinary voiding events or fecal voiding events.

24. The system of claim 23, wherein the means for controlling the means for generating and delivering electrical stimulation therapy to deliver the second electrical stimulation therapy comprises means for controlling, in response to the received input, the means for generating and delivering electrical stimulation therapy to deliver the second electrical stimulation therapy instead of the first electrical stimulation therapy.

25. The system of claim 23, wherein the means for controlling the means for generating and delivering electrical stimulation therapy to deliver the second electrical stimulation therapy comprises means for controlling, in response to the received input, the means for generating and delivering electrical stimulation therapy to deliver the second electrical stimulation therapy overlapping in time with delivery of the first electrical stimulation therapy.

* * * * *